US010107773B2

(12) United States Patent
El-Gamal et al.

(10) Patent No.: US 10,107,773 B2
(45) Date of Patent: Oct. 23, 2018

(54) METHODS AND SYSTEMS FOR HUMIDITY AND PRESSURE SENSOR OVERLAY INTEGRATION WITH ELECTRONICS

(71) Applicant: MEMS-Vision International Inc., Montreal (CA)

(72) Inventors: Mourad El-Gamal, Brossard (CA); Paul-Vahe Cicek, Montreal (CA); Frederic Nabki, Montreal (CA)

(73) Assignee: MEMS-Vision International Inc., Montreal, Quebec (CA)

( * ) Notice: Subject to any disclaimer, the term of this patent is extended or adjusted under 35 U.S.C. 154(b) by 1107 days.

(21) Appl. No.: 14/065,860

(22) Filed: Oct. 29, 2013

(65) Prior Publication Data

US 2014/0125359 A1    May 8, 2014

Related U.S. Application Data

(60) Provisional application No. 61/719,555, filed on Oct. 29, 2012, provisional application No. 61/719,558, filed on Oct. 29, 2012.

(51) Int. Cl.
| | |
|---|---|
| *H01L 29/84* | (2006.01) |
| *G01N 27/22* | (2006.01) |
| *G01L 9/12* | (2006.01) |
| *G01L 19/00* | (2006.01) |

(52) U.S. Cl.
CPC .............. *G01N 27/223* (2013.01); *G01L 9/12* (2013.01); *G01L 19/0092* (2013.01)

(58) Field of Classification Search
CPC ..................... H01L 29/84; H01L 2924/1461
See application file for complete search history.

(56) References Cited

U.S. PATENT DOCUMENTS

| | | | | |
|---|---|---|---|---|
| 2006/0105467 A1* | 5/2006 | Niksa | ................... | G01N 27/126 436/150 |
| 2009/0243063 A1* | 10/2009 | Yoon | ................... | B81C 1/00333 257/678 |
| 2011/0027930 A1* | 2/2011 | El-Gamal | ........... | B81C 1/00301 438/51 |
| 2011/0111545 A1* | 5/2011 | El-Gamal | ........... | B81C 1/00063 438/50 |

\* cited by examiner

*Primary Examiner* — Eugene Lee
(74) *Attorney, Agent, or Firm* — Rosenberg, Klein & Lee

(57) ABSTRACT

Capacitive sensors and MEMS elements that can be implemented directly above silicon CMOS electronics are disclosed. A capacitive based sensor is disposed over a first predetermined portion of a wafer that includes at least a first ceramic element providing protection for the final capacitive based sensor and self-aligned processing during its manufacturing.

14 Claims, 17 Drawing Sheets

| 110 Silicon Oxide | 120 Aluminum | 130 Sensing Material | 140 Chromium |
| 150 Silicon Nitride | 160 Silicon Carbide | 170 Parylene | 180 Silicon Carbide 2 |
| 190 Gold | 105 Silicon | | |

| 110 Silicon Oxide | 120 Aluminum | 130 Sensing Material | 140 Chromium |
| 150 Silicon Nitride | 160 Silicon Carbide | 170 Parylene | 180 Silicon Carbide 2 |
| 190 Gold | 105 Silicon | | |

| 110 Silicon Oxide | 120 Aluminum | 130 Sensing Material | 140 Chromium |
| 150 Silicon Nitride | 160 Silicon Carbide | 170 Parylene | 105 Silicon |

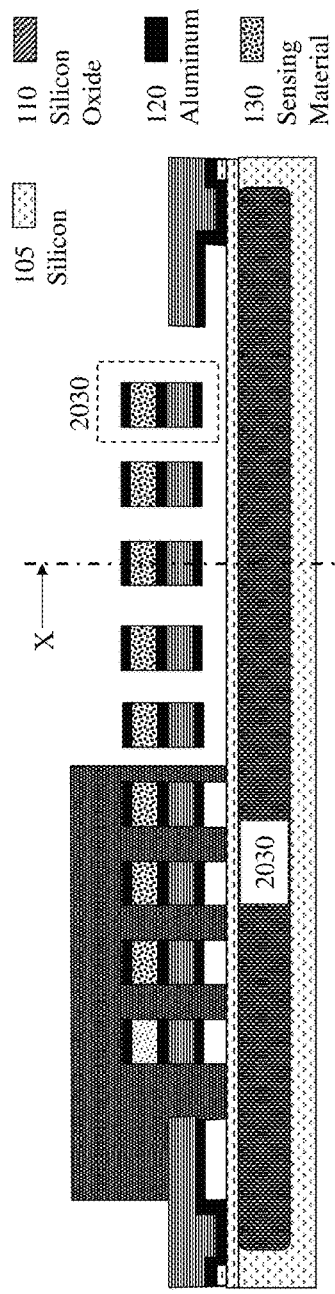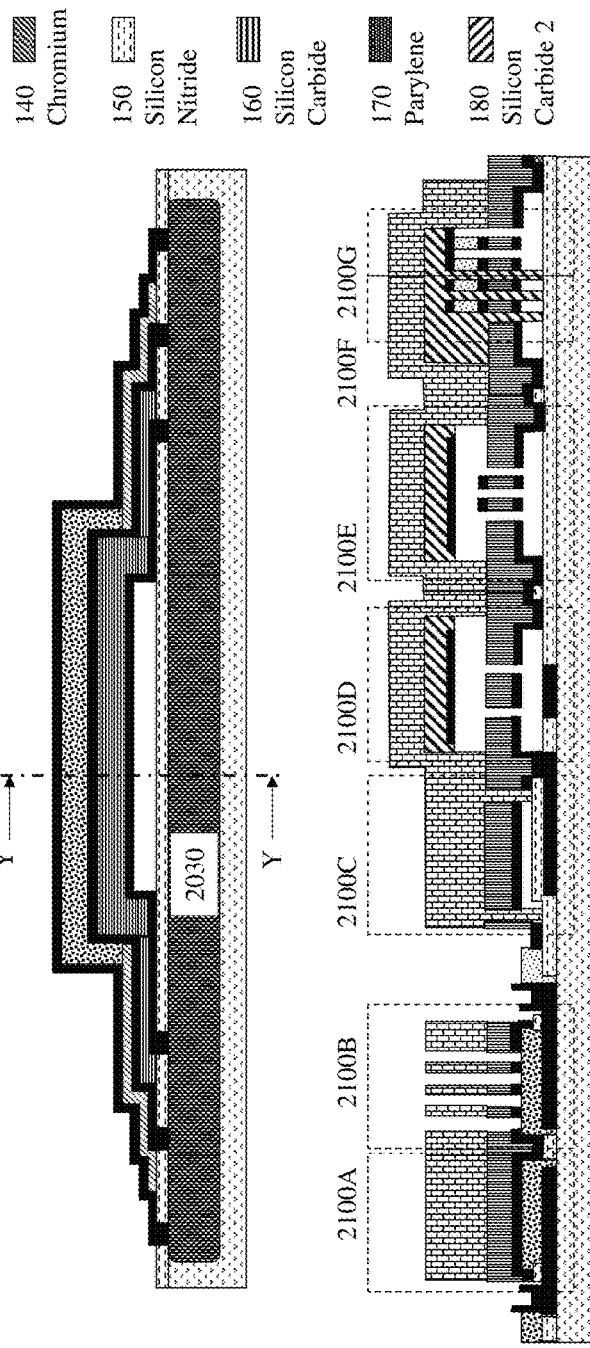
Figure 20
Figure 21

METHODS AND SYSTEMS FOR HUMIDITY AND PRESSURE SENSOR OVERLAY INTEGRATION WITH ELECTRONICS

CROSS-REFERENCE TO RELATED APPLICATIONS

This patent application claims the benefit of U.S. Provisional Patent Application 61/719,555 filed on Oct. 29, 2012 entitled "Methods and Systems for Humidity Sensor Overlay Integration with Electronics" and U.S. Provisional Patent Application 61/719,558 filed on Oct. 29, 2012 entitled "Methods and Systems for Humidity and Pressure Sensor Overlay Integration with Electronics."

FIELD OF THE INVENTION

The present invention relates to sensors and more particularly MEMS based capacitive sensors and capacitive humidity sensors which may be manufactured directly over silicon based CMOS electronics.

BACKGROUND OF THE INVENTION

Sensors are transducers or converters that measure a physical quantity and convert it into a signal which can be read. Typically, that reading is by an electronic instrument which converts the signal to a measurement based upon the sensitivity of the sensor, its calibration data, and other corrections. Included within the many types of sensors are those relating to sound, acoustics, vibration, chemicals, humidity, pressure, fluid flow, position, displacement, rotation, force, level, temperature, proximity, and acceleration. For each type of sensor, different sensing mechanisms exist which may for example be targeted to different dynamic ranges, speed, accuracy, etc. Amongst these, capacitive sensing constitutes a very important means of monitoring many environmental conditions in an effective and reliable manner as well as having applications in areas including, but not limited to, gas sensing, thickness measurements, haptic interfaces, health and fitness sensing, appliances monitoring, consumer electronics sensing, industrial sensing, building automation, wireless sensing, heating, ventilation, and air conditioning system monitoring, and displacement measurements. Accordingly, capacitive sensors have major applications in the consumer, industrial, automotive and medical fields.

It is very desirable to miniaturize and integrate such capacitive sensing systems in order to meet the requirements of existing markets and penetrate new markets and reduce fabrication costs through batch processing. Sustainable protection from oxidation, high temperatures (<350° C.) and corrosion are also especially critical for operation in harsh environments. In many instances the integration of capacitive based sensors directly with their associated electronics is important in attaining packaging dimensions and costs that are compatible with very low-cost high volume markets, such as consumer electronics for example. In addition, this integration can bring forward enhanced performance through the optimal interconnection with signal processing electronics or added functionality through the inclusion of many sensing devices, with marginal cost of system footprint.

Microelectromechanical systems (MEMS) have become a successful sensing and actuation technology. Because of their extensive optical, electrical to mechanical (and vice-versa) functionalities, MEMS devices and transducers (that convert analog environmental quantities to electrical signals) are suited to applications in many different fields of science and engineering. However, because of this vast range of functionality, MEMS fabrication processes, unlike the microelectronics industry, are difficult to gear towards general applications. As a result, most processes historically have been aimed at the fabrication of a few specific device types, and usually performance of the devices is hindered by process variability. As MEMS devices and transducers are typically sensing weak analog signals, for example pressure, acceleration, vibration, magnetic or electric fields, with capacitive based elements, there is considerable benefit in being able to tightly integrate analog front-end electronics to buffer, amplify and process these weak electronic signals and either facilitate their direct processing, such as with RF signals, or their digitization for sensing and measurements applications.

Silicon CMOS electronics has become the predominant technology in analog and digital integrated circuits. This is essentially because of the unparalleled benefits available from CMOS in the areas of circuit size, operating speed, energy efficiency and manufacturing costs which continue to improve from the geometric downsizing that comes with every new generation of semiconductor manufacturing processes. In respect of MEMS systems, CMOS is particularly suited as digital and analog circuits can be designed in CMOS technologies with very low power consumption. This is due, on the digital side, to the fact that CMOS digital gates dissipate power predominantly during operation and have very low static power consumption. This power consumption arising from the charging and discharging of various load capacitances within the CMOS gates, mostly gate and wire capacitance, but also transistor drain and transistor source capacitances, whenever they are switched. On the analog side, CMOS processes also offers power savings by offering viable operation with sub-1V power supplies and with μA-scale bias currents and below sub-μA sleep currents.

However, combining CMOS and MEMS technologies has been especially challenging because some MEMS process steps—such as the use of special materials, the need for high temperature processing steps, the danger of contamination due to the MEMS wet etching processes etc.—are incompatible with the requirements of CMOS technology. Thus, strong attention has to be paid to avoid cross contaminations between both process families. Accordingly, today MEMS processes exist that are discrete and standalone, such as Robert Bosch's (U.S. Pat. No. 5,937,275 "Method of Producing Acceleration Sensors", MEMSCAP's "Multi-User MEMS Processes" (MUMPs® including PolyMUMPs™, a three-layer polysilicon surface micromachining process: MetalMUMPs™, an electroplated nickel process; and SOI-MUMPs™, a silicon-on-insulator micromachining process), and Sandia's Ultra-planar Multi-level MEMS Technology 5 (SUMMiT V™ Fabrication Process which is a five-layer polycrystalline silicon surface micromachining process with one ground plane/electrical interconnect layer and four mechanical layers).

Other processes have been developed to allow MEMS to be fabricated before the CMOS electronics, such as Analog Devices' MOD-MEMS (monolithically integrate thick (5-10 um) multilayer polysilicon MEMS structures with sub-micron CMOS), and Sandia's iMEMS. Finally, processes have been developed to provide MEMS after CMOS fabrication such as Sandia's micromechanics-last MEMS, Berkeley Sensor & Actuator Center (BSAC), and IMEC silicon-germanium processes. Additionally DALSA Semiconductor have a highly publicized "low temperature" micro-machining with silicon dioxide process, see L. Ouellet et al (U.S. Pat. No. 7,160,752 "Fabrication of Advanced Silicon-Based MEMS Devices", Issued Jan. 9, 2007) wherein low stress structures were fabricated at temperatures between 520° C. and 570° C., being just below the temperature of eutectic formation in aluminum-silicon-copper interconnections.

However, the mechanical properties of silicon do not make it the most suitable structural material for most MEMS. Recently, silicon carbide (SiC) has generated much interest as a MEMS structural material because of its distinctive and improved properties including for example higher acoustic velocity, high fracture strength, desirable tribological properties, ability to sustain higher temperatures, and resistance to corrosive and erosive materials. To date difficulties with SiC processing have made its use non-trivial as it is non-conductive and difficult to deposit and dope at temperatures that do not damage CMOS electronics (also referred to as being CMOS-compatible temperatures). Stress control is also difficult because of the high intrinsic stresses that can develop in such a material and because if its intrinsic inertness, selective etching of SiC is difficult. As most materials are etched at a faster rate than SiC, issues arise when masking SiC for patterning and ensuring a reliable etch-stop. Whether it is for doping or for deposition, SiC processing generally has been carried-out at high temperatures and as such prior art SiC MEMS processes have not lent themselves well to CMOS integration nor to use within capacitive sensing devices that exploit materials whose properties change under exposure to the measurand, for example water vapor (humidity), methane, carbon monoxide, and other chemicals, gases, and fluids. Such materials typically have even lower maximum processing temperatures than silicon CMOS electronics. Further as most MEMS and capacitive applications require electrical signal processing, integration of MEMS to transistor-able processes, such as CMOS, is paramount.

Within the prior art, a low temperature SiC processing technique has been described by the inventors in U.S. Pat. No. 8,071,411 entitled "Low Temperature Ceramic Microelectromechanical Structures," U.S. Patent Applications 2011/0,027,930 entitled "Low Temperature Wafer Level Processing for MEMS Devices" and 2011/0,111,545 entitled "Low Temperature Ceramic Microelectromechanical Structures" and research publications including "Low-Stress, CMOS-Compatible Silicon Carbide Surface Micromachining Technology Part-I: Process Development and Characterization" (J. MEM Systems, Vol. 20, pp 720-729) and "Low-Stress, CMOS-Compatible Silicon Carbide Surface Micromachining Technology Part-II: Beam Resonators for MEMS Above-IC" (J. MEM Systems, Vol. 20, pp 730-744). The process outlined provides SiC structures with metallization formed on the upper surface of the SiC, the lower surface of the SiC, and optionally both surfaces. Typical structures within the work of the inventors in these initial publications and patents include capacitors, switches, and resonators wherein the structures included anchoring in one or more locations and electrostatic actuation.

However, as discussed supra in respect of MEMS sensors and capacitive sensors critical considerations for users include accuracy, repeatability, long-term stability, ability to recover from condensation and/or saturation, ease of calibration, resistance to chemical and physical contaminants, size, packaging, and cost effectiveness. Accordingly, it would be beneficial to exploit MEMS processes that allow for manufacturability and integration of SiC with silicon CMOS electronics, to effectively harness the benefits of SiC, and for these MEMS processes to allow integration of reference structures, electrical heaters, and electrical interconnections within the MEMS elements. It would be further beneficial for the capacitive sensors and MEMS elements to be implemented directly atop silicon CMOS electronics (i.e. above integrated circuits, or above-IC). Moreover, it would be beneficial to allow for the protection of a sensing layer by a SiC protective layer. Accordingly, the invention provides for a SiC-based MEMS process based capacitive sensing methodology. The invention providing further a route to very low-cost and high manufacturability process implementations with protection of the sensing material via SiC and above-CMOS integration capability.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to provide humidity sensors and more particularly MEMS based capacitive sensors including multiple measurand capacitive MEMS sensors which may be manufactured directly over silicon based CMOS electronics.

In accordance with an embodiment of the invention there is provided a method comprising providing a capacitive based sensor over a first predetermined portion of a wafer comprising at least a first ceramic element providing protection for the final capacitive based sensor and self-aligned processing during its manufacturing.

In accordance with an embodiment of the invention there is provided a device comprising a capacitive based sensor over a first predetermined portion of a wafer comprising at least a first ceramic element providing protection for the final capacitive based sensor and self-aligned processing during its manufacturing.

In accordance with an embodiment of the invention there is provided a method comprising providing a first capacitive based sensor for a predetermined fluid over a first predetermined portion of a wafer, the first capacitive based sensor fabricated after manufacturing of the electronic circuit and comprising at least a first ceramic element providing protection for the final fabricated first capacitive based sensor and self-aligned processing during its manufacturing and a sensing material wherein a predetermined characteristic of the sensing material varies in dependence upon the amount of the predetermined fluid thereby changing the capacitance of the sensor, and providing a second capacitance based sensor for predetermined physical parameter, the second capacitance based sensor fabricated over a second predetermined portion of the wafer; the second capacitance based sensor fabricated simultaneously with the first capacitance based sensor with the same processing sequence and comprising a predetermined portion released from the substrate, the predetermined portion being released by sacrificial etching of the sensing material beneath the predetermined portion of the second capacitance based sensor.

In accordance with an embodiment of the invention there is provided a device comprising a first capacitive based sensor for a predetermined fluid over a first predetermined portion of a wafer, the first capacitive based sensor fabricated after manufacturing of the electronic circuit and comprising at least a first ceramic element providing protection for the final fabricated first capacitive based sensor and self-aligned processing during its manufacturing and a sensing material wherein a predetermined characteristic of the sensing material varies in dependence upon the amount of the predetermined fluid thereby changing the capacitance of the sensor, and a second capacitance based sensor for predetermined physical parameter, the second capacitance based sensor fabricated over a second predetermined portion of the wafer; the second capacitance based sensor fabricated simultaneously with the first capacitance based sensor with the same processing sequence and comprising a predetermined portion released from the substrate, the predetermined portion being released by sacrificial etching of the sensing material beneath the predetermined portion of the second capacitance based sensor.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 20 depicts an alternate capacitive based fluid sensor with increased speed exploiting low temperature ceramic for mechanical support whilst enabling its integration above CMOS electronics according to an embodiment of the invention; and FIG. 21 depicts a multiple measurand sensing circuit according to an embodiment of the invention;

DETAILED DESCRIPTION

The present invention is directed to humidity sensors and more particularly MEMS based capacitive sensors which may be manufactured directly over silicon based CMOS electronics.

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims.

Figure 1:
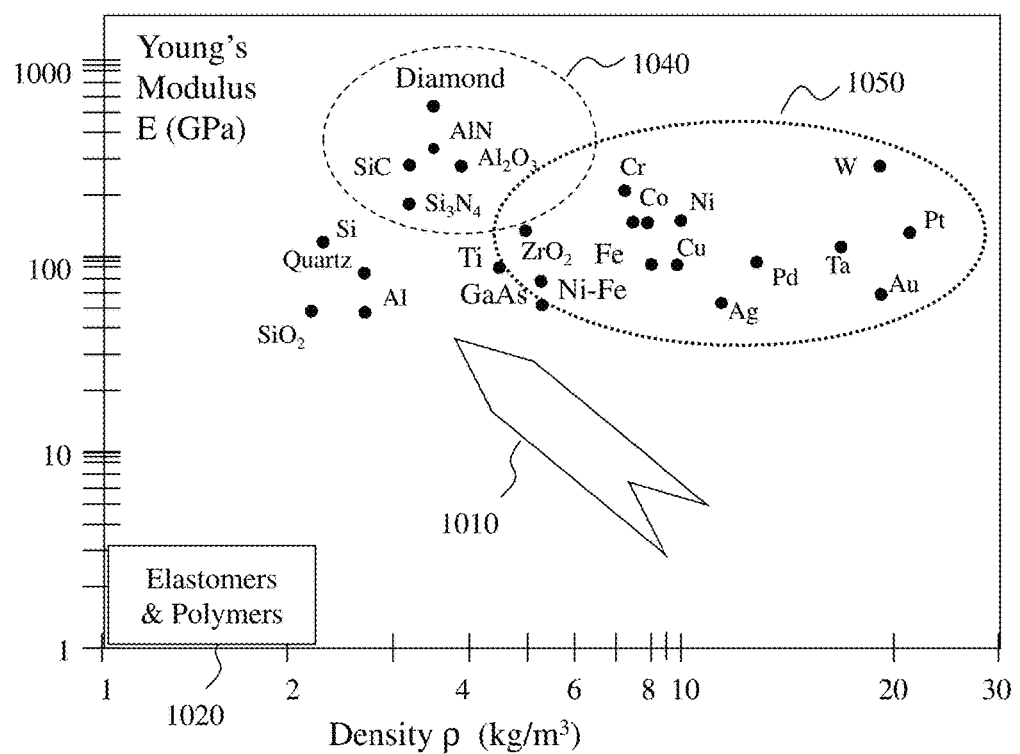
FIG. 1 illustrates the benefits of ceramics, including SiC, for MEMS device implementations over Si.

Referring to FIG. 1 shown is a material selection chart 100 for MEMS device implementations. Plotted onto the material selection chart 100 are a range of different materials including metals, dielectrics, ceramics and polymers wherein each material is represented by a point on the X-Y graph wherein the X-axis is density and Young's modulus is the Y-axis. The data being plotted is according to the work of Srikar et al "Materials Selection in Micro-Mechanical Design: An Application of the Ashby Approach" (J. Microelectromechanical Systems Vol. 10, No. 1, pp. 3-10). Young's modulus, also known as the tensile modulus, is a measure of the stiffness of an elastic material and accordingly the higher up the Y-axis a materials is the stiffer it is. The density of a material is defined as its mass per unit volume and accordingly the further to the left on the X-axis the lighter a given volume of a material is. Accordingly an ideal material for MEMS applications offering low weight, high stiffness and high hardness would sit towards the upper left of the material selection chart 100. Likewise, according to Srikar, materials offering improved resistance to hock-induced fractures are those with high strength and low density.

As evident from the material selection chart, different types of materials tend to be grouped together. Ceramic materials 1040 tending to appear in the top left, metals 1050 appearing in the middle-right, whilst polymers and elastomers 1020 are grouped together in the bottom-left. The trend arrow 1010 indicates the direction of preference for selecting materials for MEMS application in having high Young's modulus and low density. Accordingly, from material selection chart 100 better alternatives to silicon (Si) include silicon carbide (SiC), alumina ($Al_2O_3$), aluminum nitride, silicon nitride ($Si_3N_4$) or diamond (C). Of these SiC represents an interesting choice as the processing technology it requires is relatively mature. Although great strides are being made in developing nano-crystalline diamond for microsystem design, see for example Wang et al "1.51 GHz nano-Crystalline Diamond Micromechanical Disk Resonator with Material Mismatched Isolating Support" (IEEE 17th Annual Conf. on Micro Electro Mechanical Systems, 2004, pp. 641-644), the technology is still not widely available. Additionally SiC offers an increased hardness when compared with silicon, a hardness of 9 mohs versus 6.5 mohs where diamond has a hardness of 10 mohs. This increased hardness provides increased lifetime for MEMS elements such as gears, motors, translation drives, etc. Additionally SiC's high elastic modulus allows for higher resonant frequencies, hence enabling higher frequency operation of devices such as micro-mirrors, oscillators, or accelerometers, and yielding better actuation and sensing performance.

Additionally SiC does not melt at any known pressure; is highly inert chemically (making is suitable for use in harsh environments); may act as a semiconductor, wherein n-type doping may be achieved with nitrogen or phosphorus and p-type doping with aluminum, boron, gallium or beryllium; has high thermal conductivity; is superconducting below 1.5K, in 3C—SiC:Al, 3C—SiC:B and 6H—SiC:B forms; has high electric field breakdown strength; provides high maximum current density; and a very low coefficient of thermal expansion with no phase transitions that would cause discontinuities in thermal expansion. Within the prior art SiC has been traditionally deposited using one of four different methods, namely; low-pressure chemical vapor deposition (LPCVD); atmospheric pressure chemical vapor deposition (APCVD); plasma-enhanced chemical vapor deposition (PECVD); and magnetron enhanced sputtering.

Both LPCVD and APCVD have been used to successfully deposit SiC films; however, these reactions are usually highly endothermic and yield poor stress control, hence requiring deposition temperatures typically of 800° C. to 1300° C. As a result of these high temperatures, no method to date has allowed for post-CMOS integration using APCVD or LPCVD of SiC.

Furthermore, the deposition rate is typically very low since the overall reaction is limited by the surface reaction rate. PECVD which uses RF-induced plasma to transfer energy to the reactant gases allows the substrate to remain at a much lower temperature. Using this technique, low temperature deposition is possible. The composition of SiC deposited at these relatively low temperatures is amorphous or polycrystalline with crystal grains present in more quantity when the deposition temperature is increased. Residual stresses in deposited films, however, are typically very high, and therefore a CMOS incompatible post-deposition high temperature anneals is required.

For SiC deposition to provide structural layers according to embodiments of the invention, the inventors have demonstrated that by exploiting DC magnetron enhanced sputtering not only is the SiC processing essentially performed at room temperature but the processing sequence limits the maximum upper temperatures of the substrate onto which the SiC is deposited according to the processing parameters selected as discussed below. Beneficially the resulting films yield good stress control and no special CVD processes are required. DC sputtering may also be used for all metal depositions for upper and lower metallizations to the ceramic layer thereby providing for a significant minimization in the amount and cost of equipment needed to implement the manufacturing process according to embodiments of the invention as well as rendering it less hardware dependent for enhanced manufacturability.

Sputtering is typically performed, for example, by bombarding a SiC target, for example a sintered SiC target, with positive argon ions created in a plasma. These incident ions sputter away material by physical momentum transfer, which then condenses onto the substrate. Since this is a purely physical process, no external heat source is required and the actual sputtering process may be performed at room temperature. However, the substrate temperature rises marginally due to bombardment by secondary electrons, and neutral atoms. As a result according to embodiments of the invention the maximum temperature of the substrate during the SiC ceramic deposition may be limited according to the requirements of the substrate which may differ according to whether CMOS electronics are integrated for example. Accordingly, the deposition process may be established to limit the maximum upper substrate temperature for example to being below 350° C., below 250° C., below 200° C., below 150° C., and even approaching ambient temperature. These maximum temperatures being considerably lower that most CVD processes, wherein the lower upper temperature limits are achieved through a cyclic sequence of sputtering and thermal relief pauses. Beneficially, physically sputtered films are conformal in deposition profile and adhere well to the substrate. Relatively high deposition rates can be achieved and residual stresses can be nearly eliminated by careful selection of the process parameters.

Further, embodiments of the invention provide for a low temperature MEMS structural deposition process that is relatively simple, low-cost, and can be performed using only argon gas and a sintered SiC target. Beneficially the SiC from the process is amorphous, has isotropic material properties, maintains its high elastic modulus, hardness and inertness but is non-conductive thereby allowing the isolation of electrical contacts formed upon one surface or electrical contacts formed upon different surfaces of the MEMS structural element, for example between top and bottom surfaces.

Within the descriptions of embodiments of the invention methods and processes to fabricate surface-micromachined capacitive microsensors one class exploits the use of a sensing layer sandwiched between two conductive electrodes. Within this class the sensing layer provides a material whose capacitance varies with respect to an analyte of interest. Examples of sensing layers may include polymers such as cross-linked poly(methyl methacrylate-co-(2 hydroxypropyl)-methacrylate) for example, hydrophilic polymers for humidity where polymers with a weak hydrophilic site, having a low hydrogen bond propensity, may be preferred in some embodiments. In other embodiments doped and undoped oxides of aluminum, bismuth, cadmium, cerium, chromium, cobalt, copper, gallium, indium, iron, manganese, molybdenum, nickel, niobium, ruthenium, tantalum, tin, titanium, tungsten, vanadium, zinc, zirconium, and the mixed or multi-component metal oxides. They cover fluids such as $CO$, $CO_2$, $CH_4$, $C_2H_5OH$, $C_3H_8$, $H_2$, $H_2S$, $NH_3$, $NO$, $NO_2$, $O_2$, $O_3$, $SO_2$, acetone, dimethylamine (DMA), humidity, liquid petroleum gas (LPG), petrol, trimethylamine (TMA), smoke, and many others. See for example Eranna et al in "Oxide Materials for Development of Integrated Gas Sensors—A Comprehensive Review" (Critical Reviews in Solid State and Materials Sciences, Vol. 29, Iss. 3-4, pp 111-188). Other materials, with appropriate manufacturing processes may also include Si, $SiO_2$, $Si_3N_4$, SiC, and glasses with required porosity.

Other classes of surface-micromachined capacitive microsensors which may be suspended via anchored microsupports include, but are not limited to, proximity detection and/or measurement; linear and rotary position and/or measurement; dynamic motion; thickness measurement; fluid level; acceleration; vibration detection; touch sensing; and pressure. In addition to surface-micromachined capacitive microsensors surface micromachined capacitive structures may be employed as transducers including, not limited to, acoustic receiver, acoustic signal generator, ultrasonic receiver; ultrasonic generator; and switches, see for example Baxter in "Capacitive Sensors—Design and Applications" (Wiley—IEEE Press, ISBN 978-160119-0840). Capacitive structures may also be employed to provide motion through electrostatic attraction.

Beneficially, the processes are compatible with above-IC integration to make the ensuing technology viable for very low-cost applications through a system on chip (SoC) paradigm. Specifically, the fabrication processes, including all the constituent materials, as well as their processing temperatures and chemicals, allows for monolithic above-IC integration such as depicted below in respect of FIG. 6. Accordingly, embodiments of the invention support fabrication of capacitive sensing elements with integrated reference elements, heaters, etc. directly on top of the CMOS electronics to which they are electrically connected for control and sensing. Within embodiments of the invention the provisioning of a self-aligned SiC protective layer prevents damage to the electrode or sensing layers through corrosion, oxidation, mechanical effects or others, without any loss of sensing performance. This self-alignment ensures optimal sensor performance with the protection layer and reduces fabrication cost by reducing the number of required lithographic masks. An integrated reference sensor allows for reduction of the sensor's output sensitivity to temperature through compensation techniques, including but not limited to differential read-out circuitry.

Figure 2:
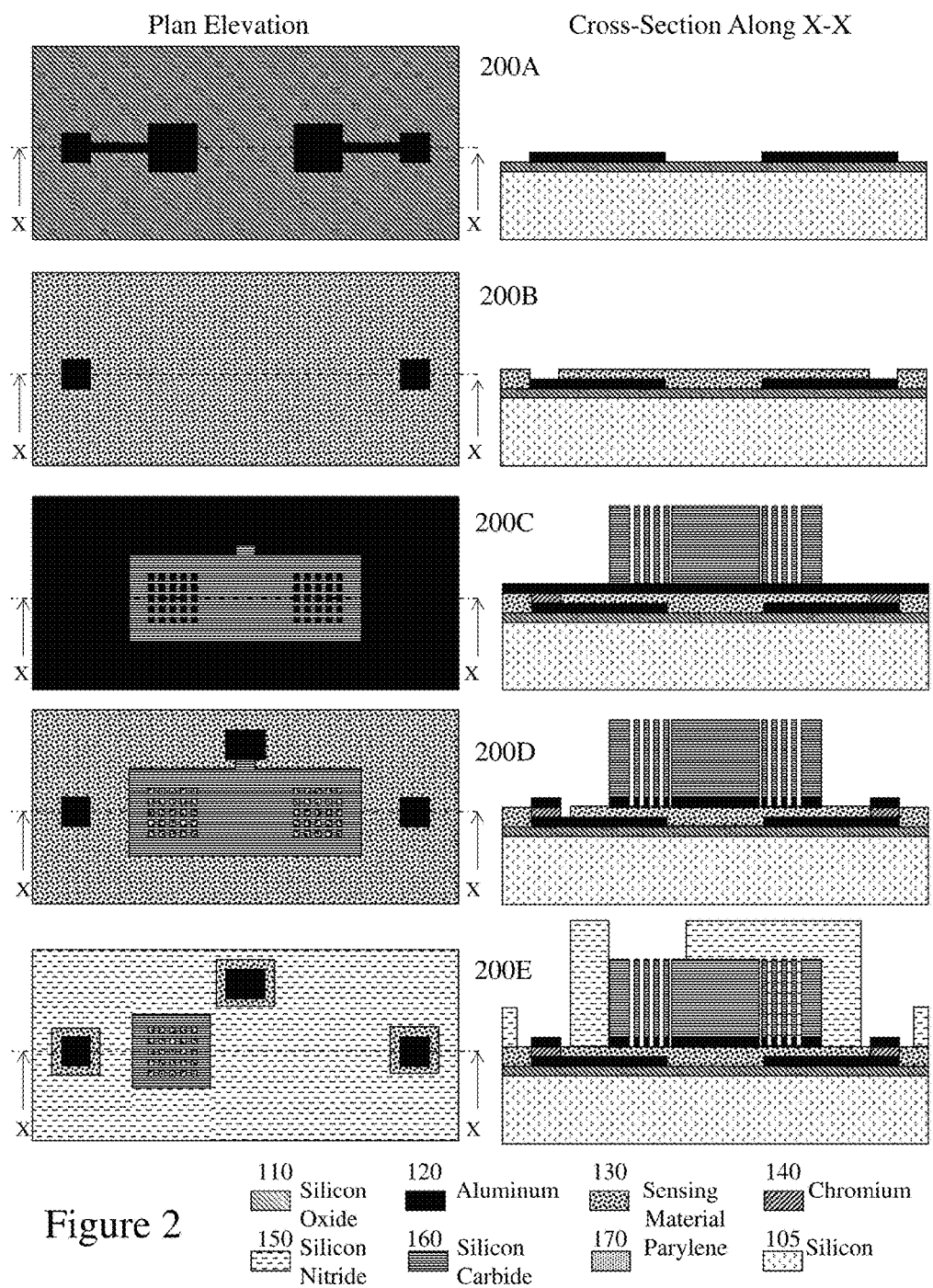
FIG. 2 depict a manufacturing sequence for providing humidity sensors and integrated reference amenable to integration atop CMOS electronics according to an embodiment of the invention.

Referring to FIG. 2 there are depicted first to third process steps 200A through 200C wherein the processing and manufacturing sequence relates to the fabrication of two electrically-connected humidity sensors. With each of the first to third process steps 200A through 200C the electrically-connected humidity sensors at these stages of processing are depicted in plan and cross-sectional views. As depicted in first process step 200A a passivated silicon 105 substrate, passivated with silicon dioxide ($SiO_2$) 110 has a first layer of metallization deposited, for example 120 nm of DC sputtered aluminum (Al) 120, and etched through wet or dry processing form the bottom sensing electrode. The silicon 105 substrate, not identified explicitly, may for example comprise CMOS electronics or not. According to embodiments of the invention where the silicon 105 substrate contains CMOS electronics the fabrication of two electrically-connected humidity sensors may be performed directly on top of the CMOS electronics, adjacent to the CMOS electronics, or partially overlapping the CMOS electronics.

Next in second process step 200B a sensing layer, e.g. 200 nm of Sensing Material 130, is deposited, and dry etched to form vias for electrical pads. Next a stack of metals and ceramic layers are applied through DC sputtering processes, as depicted in third process step 200C to provide the top sensing electrode and the protective layer. The metals constitute the electrode and pads, for example these comprise a 10 nm chromium (Cr) 140 adhesion layer and a 300 nm Al 120 conductive layer. The ceramic layer(s), for example 2 μm SiC 160 deposited by DC magnetron enhanced sputtering, will provide a protective layer to the two electrically-connected humidity sensors. In order to provide reliable device operation through self-alignment manufacturing and to reduce the number of masks required, the ceramic SiC 160 layer(s) is (are) etched first using reactive ion etching (RIE) for example such that the etching process terminates at the top metal layer, in this instance the 300 nm Al 120 conductive layer, thereby forming the geometry of the protective layer.

The SiC 160 ceramic layer then serves as a hard mask for the etching of the underlying metals, so as to form the top electrode. To reduce the number of necessary layers in the process, electrical pads are also defined with the same top metal layers; through lithography as depicted in fourth process step 200D in FIG. 2 Accordingly at this point two self-aligned ceramic MEMS style electrically-connected humidity sensors are formed atop the silicon 105 substrate with the integral CMOS electronics. It would be evident that the metallization processes described providing surface contactable pads may support for example the interconnection of CMOS electronics and the electrically-connected humidity sensor(s) through wire or tape bonding such as ball bonding, wedge bonding, thermocompression bonding, etc. Alternatively, the metallization processes at the initial stages of manufacturing, such as represented in first process step 200A may be modified to provide via type electrical interconnections to the CMOS through the passivation layer. It would also be evident that more complex passivation/electrical interconnection sequences may be implemented without departing from the scope of the invention.

Fifth processing step 200E in FIG. 2 depicts the two electrically-connected humidity sensors after application of a hermetic sealing layer, for example a 2 μm parylene 170 layer deposited by chemical vapour deposition (CVD). Openings are dry etched into this parylene 170 layer to access the electrical pads and clear all active devices which are not intend to form reference structures. As evident within fifth process step 200E of the two electrically-connected humidity sensors one (right hand side) is isolated with the parylene 170 layer whereas the other (left hand side) is exposed to ambient environment. It would also be evident that other hermetic sealing may be applied including, but not limited to, plasma SiC (e.g. deposited from non-pyrophoric trimethylsilane), sputtered SiC, plasma or sputtered silicon nitride or oxide noble metal (e.g. gold), atomic or molecular layer depositions, spin-on glass (SOG), barrier metals (e.g. $TiW_xN_{1-x}$) or combinations thereof. This hermetic enclosure of one of the sensing elements allows for it to be used as a reference to decouple any common-mode drift effects (e.g. temperature) using differential measurement. It would be evident to one skilled in the art that in some embodiments of the invention sealing options may vary according to design restrictions such that for example where the sensing layer is etched through, such as described below in respect of FIG. 5 that conductive sealing materials may not be employed, e.g. low frequency AC or DC capacitance measurements, or their properties defined to not impact measurements, e.g. high frequency AC measurements.

Figure 3A:
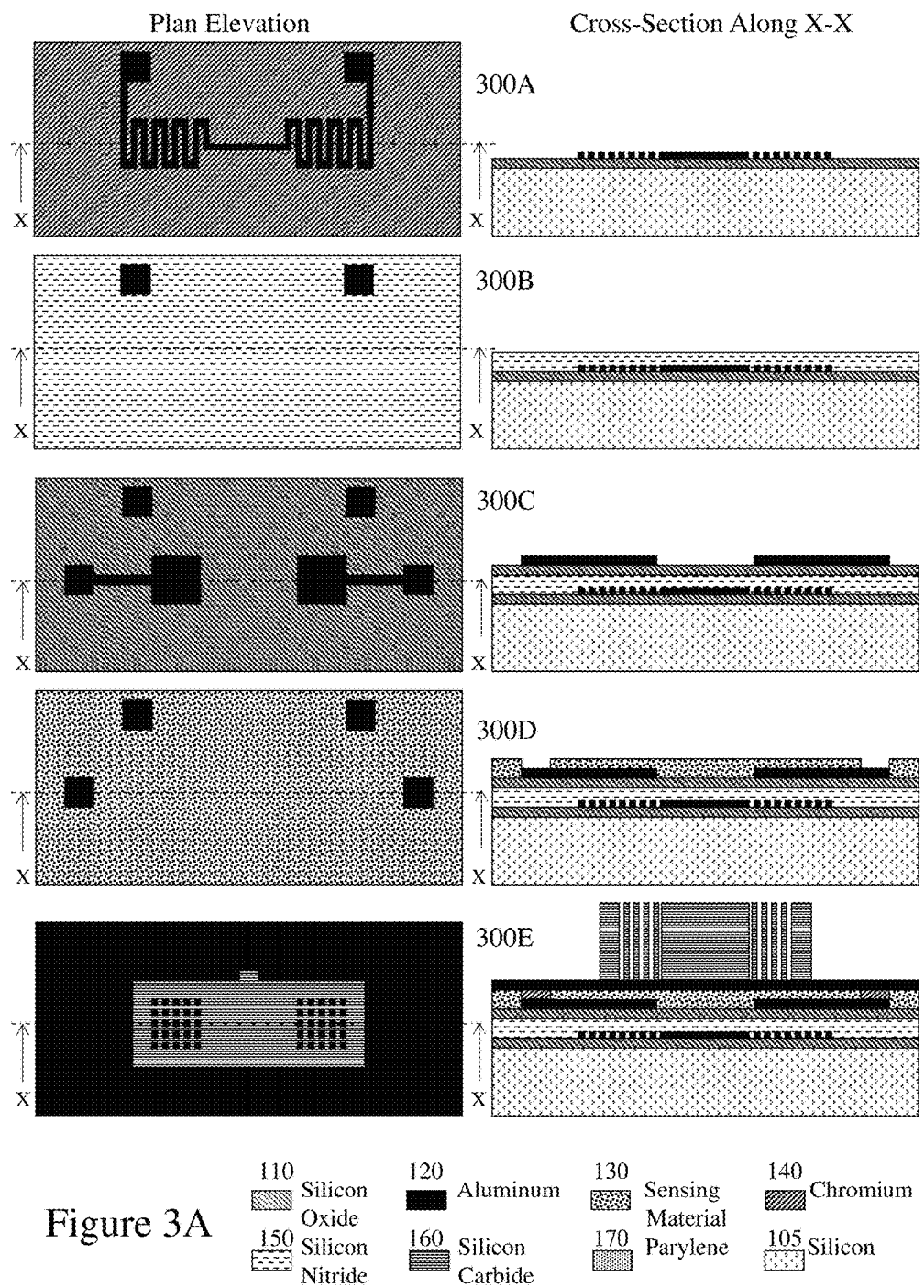
FIGS. 3A and 3B depict a manufacturing sequence for providing a humidity sensor integrated reference, and integrated heater amenable to integration atop CMOS electronics according to an embodiment of the invention.

Now referring to FIG. 3A there are depicted first to fourth process steps 300A through 300D wherein the processing and manufacturing sequence relates to the fabrication of two electrically-connected humidity sensors with integrated heater structures. With each of the first to fourth process steps 300A through 300D the electrically-connected humidity sensors at these stages of processing are depicted in plan and cross-sectional views. According to first process step 300A an initial metallization layer, e.g. 60 nm Al 120 is deposited by DC sputtering, and patterned through wet or dry etching to form a pair of interconnected electrical heater elements. Next in step 300B these heater elements are covered by a passivation layer, for example 100 nm of plasma enhanced CVD (PECVD) deposited silicon nitride ($Si_3N_4$) 150, which is itself patterned by dry etching to form vias to electrically connect the heater elements subsequently. Next in third process step 200C the part processed silicon 105 substrate is passivated with $SiO_2$ 110 and a second layer of metallization, for example 120 nm of DC sputtered Al 120, is deposited and etched through wet or dry processing to form the bottom sensing electrode. Next in fourth process step 300D a polymeric sensing layer, e.g. 200 nm of Sensing Material 130, is deposited, and dry etched to form vias for electrical pads.

Next in fifth to seventh process steps 300E through 300G the process flow follows the same sequence as described above in respect of third to fifth process steps 200C through 200E in FIG. 2. Accordingly a stack of metals and ceramic layers are applied through DC sputtering processes to provide the top sensing electrode and the protective layer, for example these comprise a 10 nm Cr 140 adhesion layer and a 300 nm Al 120 conductive layer together with a 2 μm SiC 160 layer; the SiC 160 is etched terminating at the top 300 nm Al 120 thereby forming the geometry of the protective layer; the underlying metals are etched using the SiC 160 ceramic layer as a hard mask; and a 2 μm parylene 170 layer is deposited and dry etched wherein the openings access the electrical pads and clear all active devices which are not intend to form reference structures.

Accordingly first to seventh process steps 300A through 300G provide for two electrically-connected humidity sensors, one isolated (right hand side) from the ambient environment by the parylene 170 layer and hence acting as a reference element and the other (left hand side) exposed to the ambient environment. The inclusion of the thin film heaters within first and second process steps 300A and 300B provides, for example, for operation of the two electrically-connected humidity sensors at an elevated set-point temperature wherein active control allowing variations of temperature to be removed from the measurements or for thermal cycling of the structure in order to periodically dry or reduce the moisture content within the Sensing Material 130 sensing layer or to enhance the recovery time of the sensor to elevated or prolonged humidity exposures.

Figure 3B:
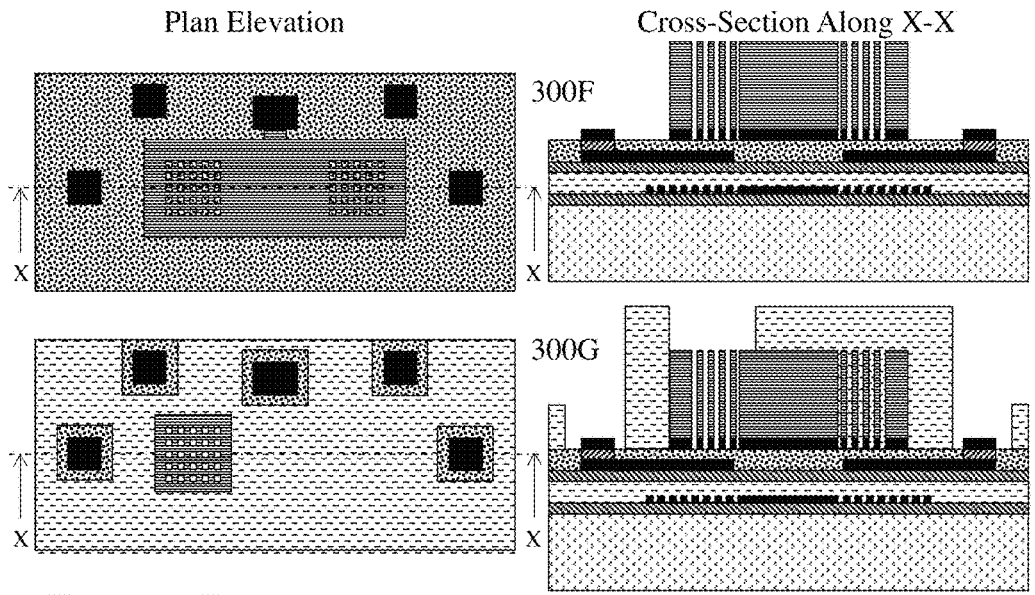
Figure 4:
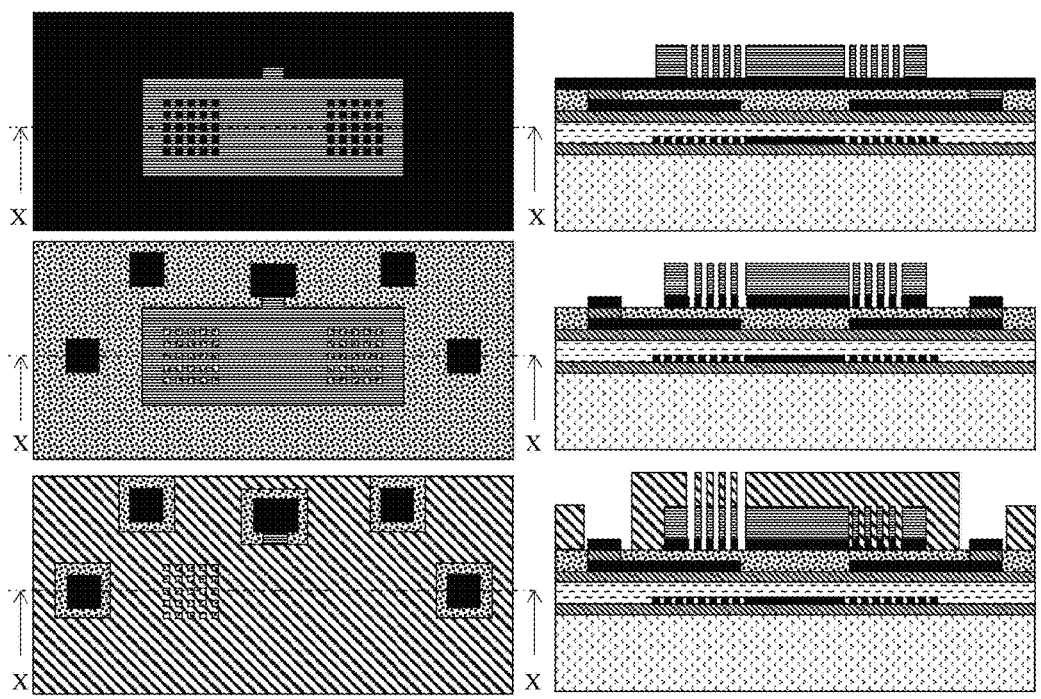
FIG. 4 depicts an alternate back-end process flow for providing a humidity sensor, integrated reference circuit and integrated heater amenable to integration atop CMOS electronics according to an embodiment of the invention.

Now referring to FIG. 4 there are depicted first to third process steps 400A through 400C wherein the processing and manufacturing sequence relates to the fabrication of two electrically-connected humidity sensors with integrated heater structures. First process step 400A depicts the processing sequence at an equivalent point to third process step 200C in FIG. 2 or fifth process step 300E in FIG. 3B but wherein a first SiC layer, SiC1 160, used to provide a protective layer for the two electrically-connected humidity sensors has been deposited at a reduced thickness to that in either third process step 200C in FIG. 2 or fifth process step 300E in FIG. 3B. As with the preceding process flows the first to third process steps 400A through 400C show the electrically-connected humidity sensors at these stages of processing in plan and cross-sectional views.

Next in second step 400B the self-aligned etching of the metallization using the first SiC layer is undertaken before a second SiC layer, SiC2 180, is deposited and patterned thereby opening one humidity sensor of the device to the ambient environment whilst the second humidity sensor is now covered and sealed, as shown in step 400C. Accordingly second SiC layer, SiC2 180, may be plasma SiC or sputtered SiC providing a barrier to moisture as well as chemical resistance, corrosion resistance, and mechanical protection. Optionally, a metallization layer or layers may be employed in conjunction with the second SiC layer, SiC2 180.

Figure 5:
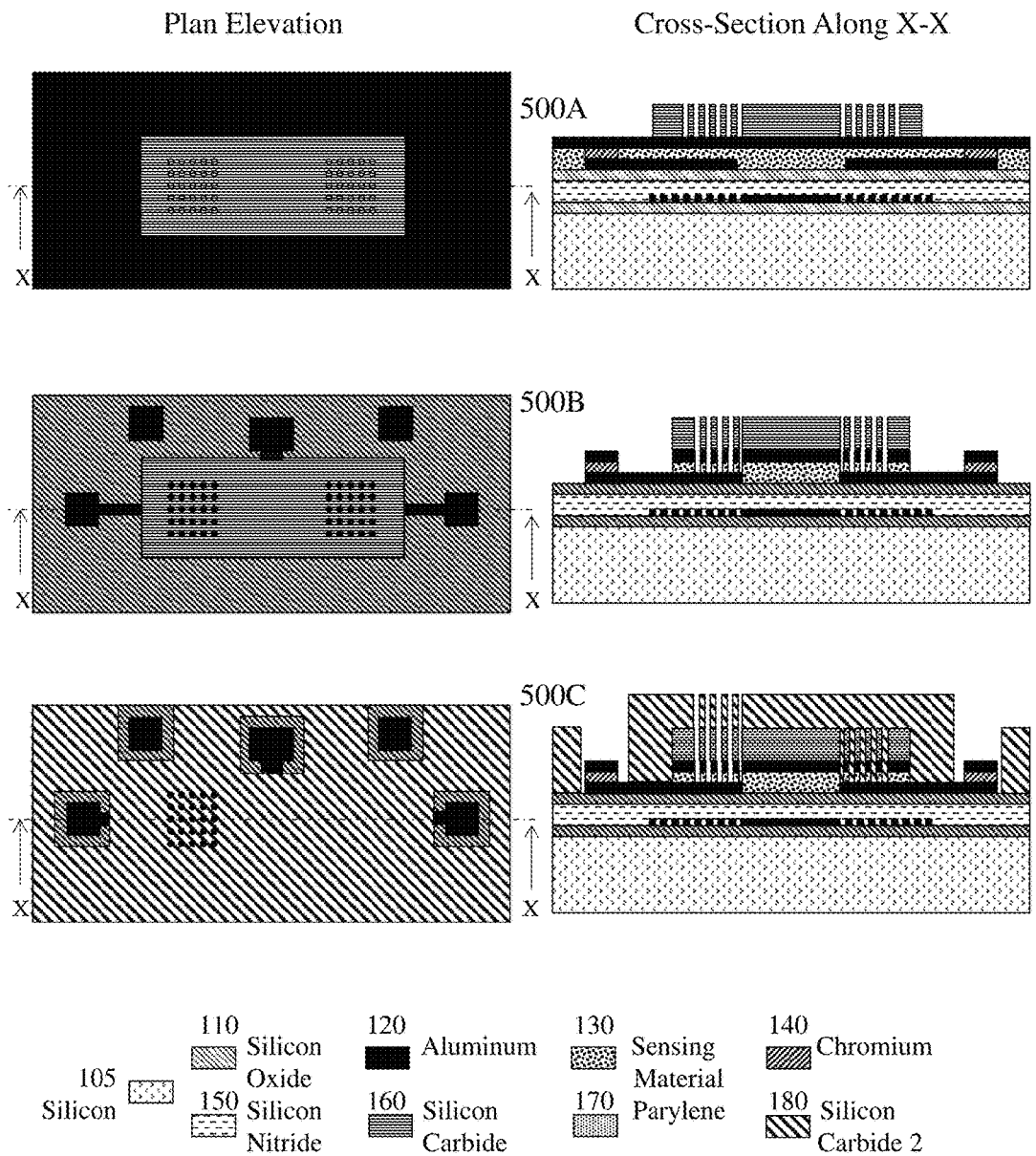
FIG. 5 depicts an alternate back-end process flow for providing a fast humidity sensor, integrated reference circuit and integrated heater amenable to integration atop CMOS electronics according to an embodiment of the invention.

Now referring to FIG. 5 there are depicted first to third process steps 500A through 500C wherein the processing and manufacturing sequence relates to the fabrication of two electrically-connected humidity sensors with integrated heater structures. First process step 500A depicts the processing sequence at an equivalent point to third process step 200C in FIG. 2, fifth process step 300E in FIG. 3B, and first process step 400A in FIG. 4 wherein the first SiC layer, SiC1 160, has been again been deposited at a reduced thickness. As with the preceding process flows the first to third process steps 500A through 500C show the electrically-connected humidity sensors at these stages of processing in plan and cross-sectional views.

Next in second step 500B the self-aligned etching of the metallization using the first layer is undertaken but now the self-aligned etching is progressed further to etch into the polymeric sensing layer comprising for example 200 nm of Sensing Material 130. Then in third process step a second SiC layer, SiC2 180, is deposited and patterned thereby opening one humidity sensor of the device to the ambient environment whilst the second humidity sensor is now covered and sealed. As with the preceding embodiments of the invention the second SiC layer may be plasma or sputtered SiC layer, parylene 170, or other material or combination of materials providing a barrier to isolate the reference sensor element from the ambient environment. In comparison to FIG. 4 it would be evident that isolation of the Sensing Layer 130 is achieved through the second SiC layer, SiC2 180, at the sides/edges of the Sensing Layer 130.

Referring to FIGS. 2, 3, and 4 the sensing layer, depicted by Sensing Material 130, but as noted supra capable of being one of a plurality of alternate materials supporting a variety of gas sensors, is provided in film form between the electrodes of the capacitor wherein in FIG. 5 the additional self-aligned etching through the Sensing Material 130 results in an array of sensing layer elements between the electrodes. As depicted in FIG. 5 the openings within the SiC layer have a geometry such that the sensing layer elements are cylindrical. The response time of a humidity sensor is dictated on the one hand by the choice of hygroscopic material as the higher the moisture diffusion constant of the sensing layer the faster the capacitance will adjust to changes in ambient humidity. However, once the material is chosen the speed, response time, can only be enhanced by modifying the geometry of the film. In most instances the materials of choice are restricted by a combination of the gas or fluid to be sensed and the processing requirements of manufacturing the sensors. Accordingly diffusion coefficients, D, are typically $10^{-9} \leq D \leq 10^{-8}$ $cm^2s^{-1}$.

For a planar film the normalized capacitance is a function of $Dt/L^2$ so that the response time is proportional to the square of the film thickness, L, and inversely proportional to the diffusion constant, D. In contrast the normalized capacitance for a cylindrical body is a function of $Dt/r^2$ such that now the response time is proportional to the square of the radius, r, whilst still being inversely proportional to the diffusion constant, D. Accordingly, the designer of the sensor may accord the material selected and its diffusion coefficient, D, in conjunction with considerations of manufacturing processes may elect to employ either a planar film or pillar based design.

Figure 6:
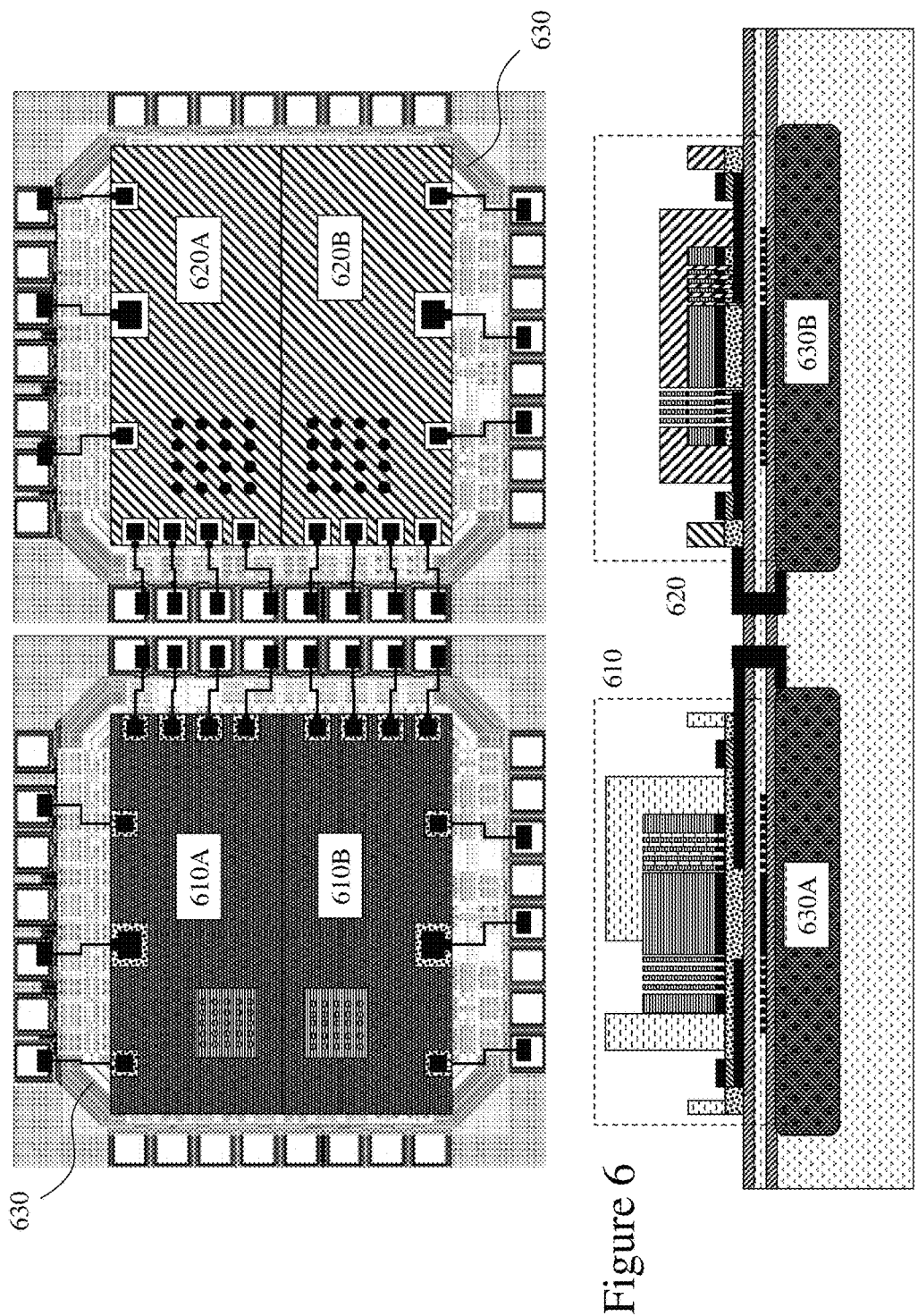
FIG. 6 depicts an exemplary layout for a multi-element capacitive sensor with integrated reference elements fabricated according to an embodiment of the invention.

Referring to FIG. 6 there is depicted a schematic of the above-IC nature of embodiments of the invention wherein a CMOS circuit comprises at least a pair of sensor interface circuits 630A and 630B respectively. One sensor interface circuit 630A is electrically connected to first and second dual electrically-connected humidity sensors 610A and 610B respectively whilst the other interface circuit 630B is electrically connected to third and fourth dual electrically-connected humidity sensors 620A and 620B respectively. As depicted each of the first and second dual electrically-connected humidity sensors 610A and 610B respectively are of first design for the humidity sensor elements and third and fourth dual electrically-connected humidity sensors 620A and 620B respectively are of a second design for the humidity sensor elements although all four included integrated reference elements. Accordingly the circuit allows integral heaters within a dual electrically-connected humidity sensors of one of the first or second designs to be activated on one circuit whilst the other maintains humidity sensor measurements. As depicted in the cross-section each of the first and second designs are directly integrated above the interface circuits 630A and 630B respectively by virtue of the low temperature manufacturing processes which limit the maximum exposure of the CMOS circuit, according to the specific manufacturing process, to 350° C., 300° C., 250° C., 200° C., or lower.

Figure 7:
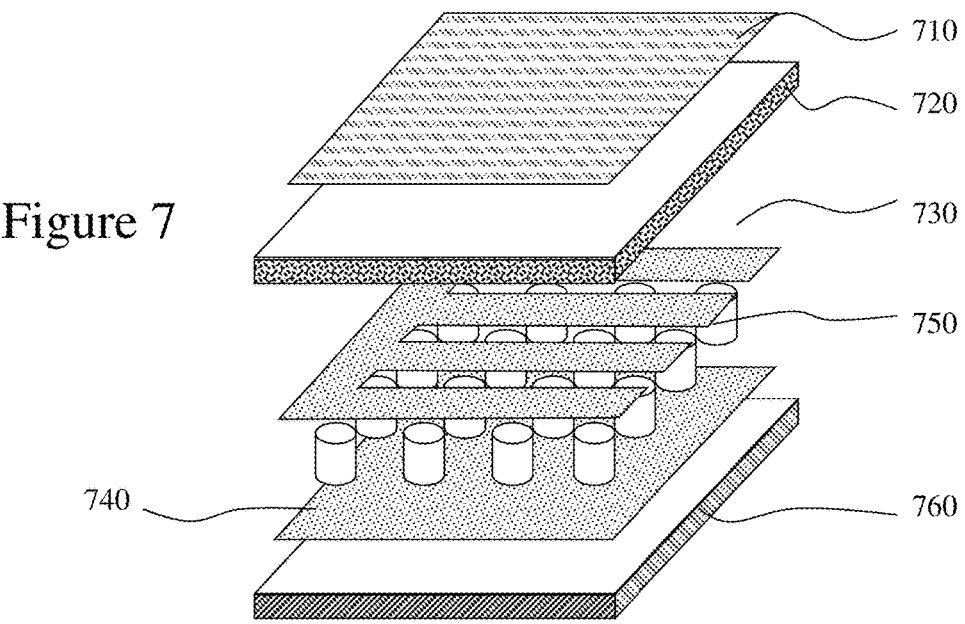
FIG. 7 depicts an alternate electrode geometry according to an embodiment of the invention for fast capacitive sensor elements to reduce stray capacitance effects within the sensor and reference elements.

Now referring to FIG. 7 there is depicted an exploded three-dimensional perspective view of the capacitor sensor section of a sensing circuit according to an embodiment of the invention wherein a plurality of sensing elements 750 are disposed between a lower electrode plane 740 and upper electrode 730 which sits atop a dielectric layer 760. Also disposed above the upper electrode is a second dielectric 720 wherein the fluid flow is now parallel to the lower electrode plane 740 rather than being perpendicular to the sensing material plane as depicted in FIGS. 2 through 6 respectively. Such a flow may for example occur where the sensing element is integrated into a microfluidic circuit rather than sensing the ambient environment. However, such a design may be impacted from the capacitance between the lower electrode plane 740 and upper electrode 730 arising from the regions without the sensing material, e.g. which are air-filled in the case of a humidity sensor. Accordingly, the upper electrode 730 is patterned such that it does not cover the tops of any of the sensing columns and a second upper electrode 710 is disposed on top of a third dielectric layer 720. This structure separates the capacitance of the air-gap from that of the sensing layer in its pillar form. The upper electrode 730, which acts as a guard electrode, and second upper electrode 710 are maintained at the same potential in order to create a homogenous electric field between the lower electrode plane 740 and the upper electrode 730/second upper electrode 710 combination. The capacitance of the sensing layer, in the form of sensing elements 750, is selectively extracted by applying an AC voltage across the lower electrode plane 740 and the upper electrode 730/ second upper electrode 710 and measuring the current flowing through the second upper electrode 710. As a result, the gap capacitance is excluded so that the sensor capacitance does not drift even if particles become trapped inside or near the gaps.

It would be evident that within the descriptions of embodiments of the invention in respect of FIGS. 2 through 7 that the descriptions have been primarily described with respect to humidity sensors. However, it would be evident that embodiments of the invention may be implemented based upon the appropriate sensing layer, such as described supra, which may include for example doped or undoped oxides of aluminum, bismuth, cadmium, cerium, chromium, cobalt, copper, gallium, indium, iron, manganese, molybdenum, nickel, niobium, ruthenium, tantalum, tin, titanium, tungsten, vanadium, zinc, zirconium, mixed or multi-component metal oxides, and polymers that other materials may be sensed through the capacitive sensor approach.

Within the embodiments of the invention described above in respect of FIGS. 2 through 7 the reference capacitive sensing element has been described as being hermetically sealed through the use of one or more materials including but not limited to SiC, parylene, silicon nitride or oxide, noble metals, atomic or molecular layer depositions, spin-on glass, and barrier metals. It would be evident that the degree of hermeticity may vary in dependence upon one or more factors including, but not limited to, the fluid being sensed; the ceramic composition, porosity, thickness etc.; the sensor geometry; operating environment; anticipated lifetime of sensor; acceptable failure rate; and acceptable calibration error.

Figure 8:
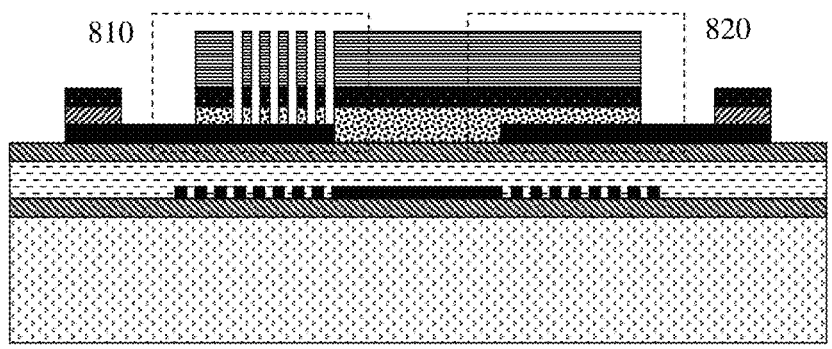
FIG. 8 depicts an exemplary layout for a humidity sensor and integrated reference circuit integrable atop CMOS electronics according to an embodiment of the invention.

Also as discussed supra available sealing options may vary according to design restrictions such that for example where the sensing layer is etched through, such as described below in respect of FIG. 5 that conductive sealing materials may not be inappropriate. Accordingly in some embodiments of the invention, such as depicted in FIG. 8, the reference capacitive sensing element 820 is formed during the same manufacturing sequence as the capacitive sensing element 810 but without patterning such that the ceramic, e.g. SiC, acts as the barrier without additional processing or is patterned directly thereover with a noble metal or barrier metal, such as gold 190 for example. As the surface area of the reference capacitive sensing element 820 now differs from that of the capacitive sensing element 810 an adjustment of the calibration derived from the reference capacitive sensing element 820 by the CMOS electronics may be implemented or the area of the reference capacitive sensing element 820 may be adjusted accordingly to make them approximately equivalent.

Figure 9A:
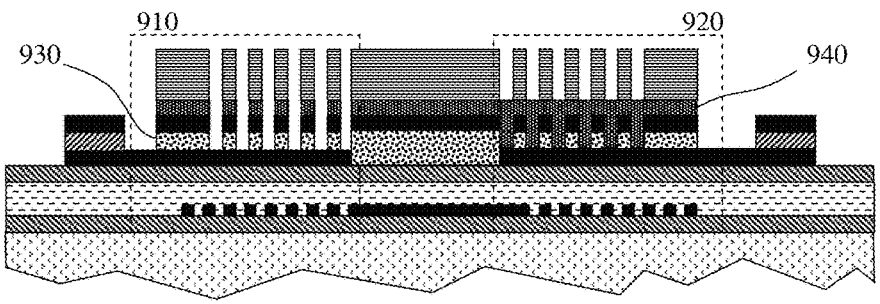
FIGS. 9A and 9B depict exemplary layouts for humidity sensor and integrated reference circuits integrable atop CMOS electronics according to embodiments of the invention.

Now referring to FIG. 9A a humidity sensor 910 with integrated reference circuit 920 are depicted wherein the manufacturing sequence progressed exploiting processes and process steps similar to those described supra in respect of FIGS. 2 through 5 except that prior to the deposition of the ceramic layer SiC, SiC1 160, a parylene 170 layer was deposited such that it sits atop the barrier, gold 190, and beneath the ceramic layer, SiC1 160. As depicted therefore humidity sensor 910 comprises the sensing layer 930, Sensing Material 130, and parylene layer 940, parylene 170, both of which have been patterned thereby allowing humidity migration into the active sensing layer 930. The integrated reference circuit 920 similarly comprises a patterned sensing layer 930, Sensing Material 130, whilst the parylene layer 940, parylene 170, has not been patterned and conformally coats and seals the sensing layer 930. Subsequently, the ceramic, SiC1 160, was deposited and patterned. In this instance the ceramic, SiC1 160, was similarly patterned on both the humidity sensor 910 and the integrated reference circuit 920. This may for example be employed where the capacitance of the two circuits is influenced by the structure of the ceramic layer, SiC1 160.

Figure 9B:
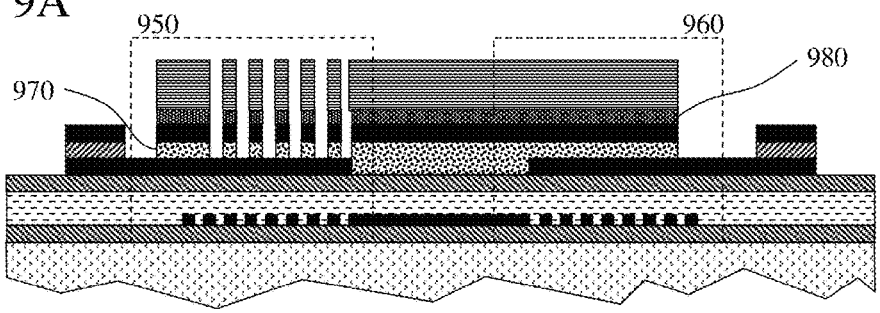

Now referring to FIG. 9B there are depicted a humidity sensor 950 with integrated reference circuit 960 wherein the manufacturing sequence progressed exploiting processes and process steps similar to those described supra in respect of FIGS. 2 through 5 except that prior to the deposition of the ceramic layer SiC, SiC1 160, a parylene 170 layer was deposited such that it sits atop the barrier, gold 190, and beneath the ceramic layer, SiC1 160. As depicted therefore humidity sensor 950 comprises the sensing layer 970, Sensing Material 130, and parylene layer 980, parylene 170, both of which have been patterned thereby allowing humidity migration into the active sensing layer 970. The integrated reference circuit 960 similarly comprises a patterned sensing layer 970, Sensing Material 130, and parylene layer 980, parylene 170, but neither has been patterned. Subsequently, the ceramic, SiC1 160, was deposited and patterned. In this instance the ceramic, SiC1 160, patterned within the humidity sensor 950 is depicted as being narrower than the sensing and parylene layers 970 and 980 respectively and the barrier layer. Accordingly, in this instance this offset exposes increased parylene 170 in the parylene layer 980 thereby allowing this to provide a hydrophobic layer protecting the humidity sensor 950 from water droplets but without blocking the humidity sensing sensing layer 970. In FIG. 9A the parylene layer 940 provided for improved sealing of the integrated reference circuit 920.

It would be evident to one skilled in the art that the barrier may be implemented with one or more other barrier materials and/or noble metals, such as gold 190 for example. It would also be evident that parylene layers 940 and 980 in FIGS. 9A and 9B respectively may be replaced with another material according to the requirements of the design which may include for example improved moisture sealing, such as described supra in respect of FIG. 9A, or hydrophobic properties, such as described supra in respect of FIG. 9B. Optionally, the barrier may be eliminated.

Figure 10:
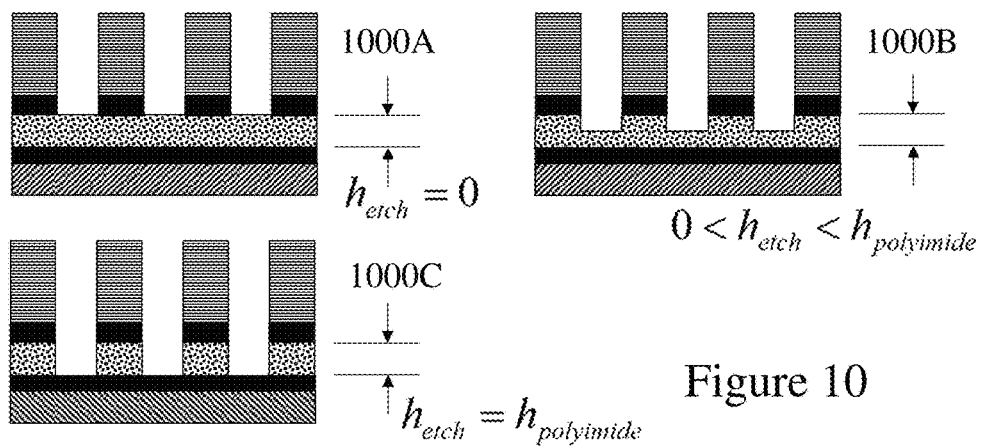
FIG. 10 depicts variations in humidity sensors according to embodiments of the invention wherein performance may be tuned through varying etch depth of the humidity sensing layer.
Figure 11:
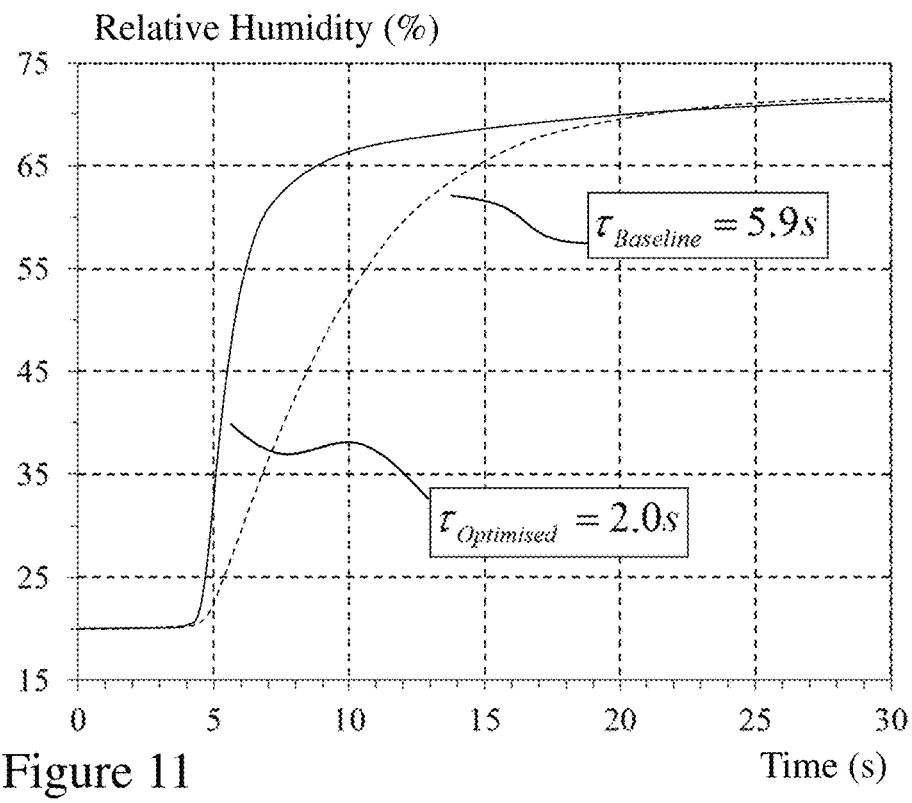
FIG. 11 depicts the reduced time constant for a humidity sensor according to an embodiment of the invention wherein performance is tuned through etch depth of the humidity sensing layer.

Within the preceding FIGS. 2 through 9 the sensing material has been depicted as fully etched or unetched. However, as evident from FIG. 10 in first to third images the Sensing Material 130 may be unetched, partially etched, or fully etched respectively. According to the requirements of the humidity sensor performance and the humidity sensing material employed this etching may be varied to augment sensor sensitivity and/or response time by adjusting the moisture area of contact and/or adjusting the path to the active sensor region. Such a reduction of response time, time constant, is depicted in FIG. 11 from an initial 5.9 second baseline time constant for an unetched sensing layer to 2.0 seconds for an optimized design via etching variation.

Figure 12:
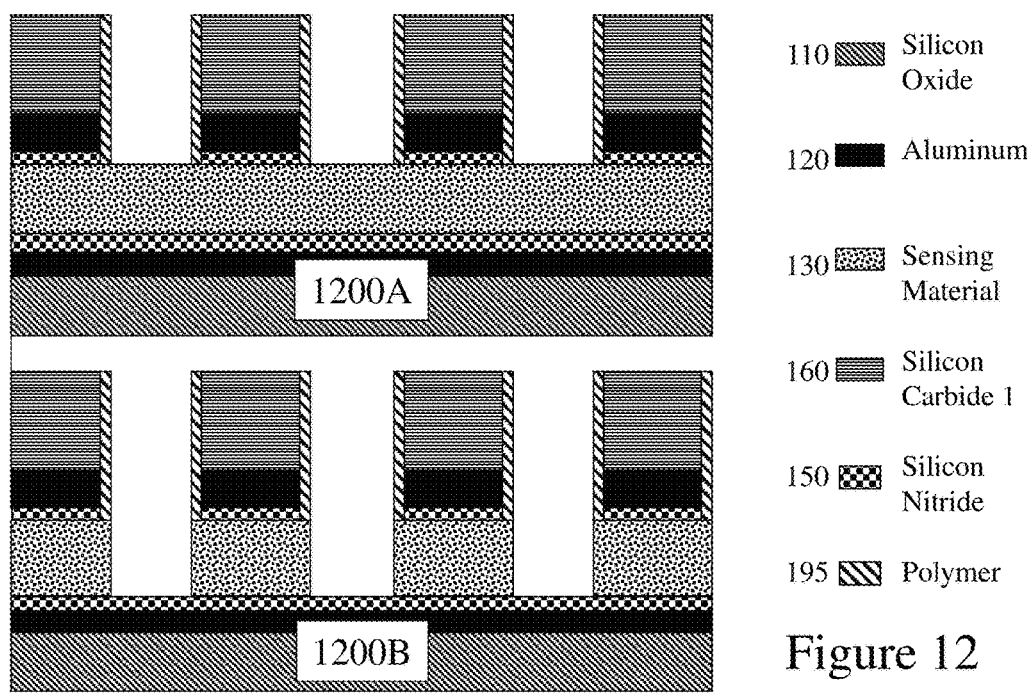
FIG. 12 depicts humidity sensor active regions according to embodiments of the invention to reduce corrosion of the electrodes.

Amongst the issues for humidity sensors is corrosion from the moisture either alone or in combination with other chemicals within the environment being monitored, Referring to FIG. 12 there are depicted cross-sections of first and second humidity sensor active regions 1200A and 1200B respectively according to embodiments of the invention. Within first and second humidity sensor active regions 1200A and 1200B respectively protection for the electrodes is provided by a combination of vertically protecting the upper surface of the bottom metal electrode and the lower surface of the top electrode from corrosion using a first ceramic layer, e.g., silicon nitride 150, and the upper surface of the upper electrode with a second ceramic layer, e.g. silicon carbide 160. Additionally, horizontal protection for the laterally exposed surfaces of the top electrode can be provided by applying, for example, a chemical vapor deposited (CVD) conformal polymer layer, polymer 195. Polymer 195 may, for example, be Teflon or plasma-induced polymerization of octafluorocyclobutane (C4F8) with subsequent processing to remove the horizontal sections using directional (anisotropic) plasma etching (e.g. reactive-ion-etching) to leave a sidewall protection without impeding moisture access to the sensing layer. As depicted in second humidity sensor active region 1200B this protection method is also suitable for subsequent etching of the exposed sensing material.

Figure 13:
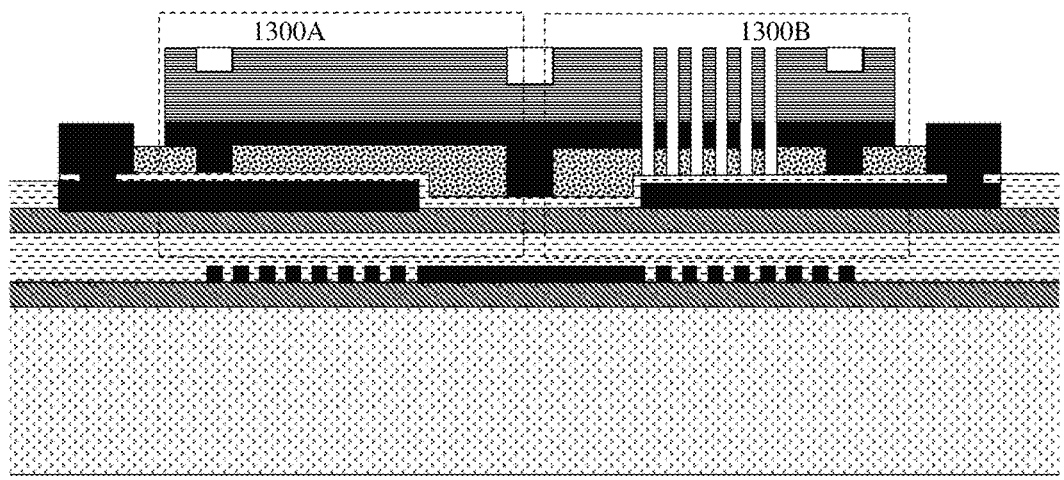
FIG. 13 depicts a humidity sensor incorporating a sealed integrated reference circuit according to an embodiment of the invention.

With respect to an integrated reference circuit then in FIG. 13 there is depicted a humidity sensor incorporating a sealed integrated reference circuit 1300A in conjunction with the active humidity sensor 1300B according to an embodiment of the invention. Accordingly, as depicted the sensing layer, Sensing Material 130, is sealed between the upper and lower electrodes, aluminum 120, wherein a passivation layer, e.g. silicon nitride 150, deposited upon the lower electrode prevents electrical shorting of the top and bottom aluminum electrodes. Within the active humidity sensor 1300B such a sealing eliminates alternate moisture ingress routes except the desired active region of the active humidity sensor 1300B.

Figure 14A:
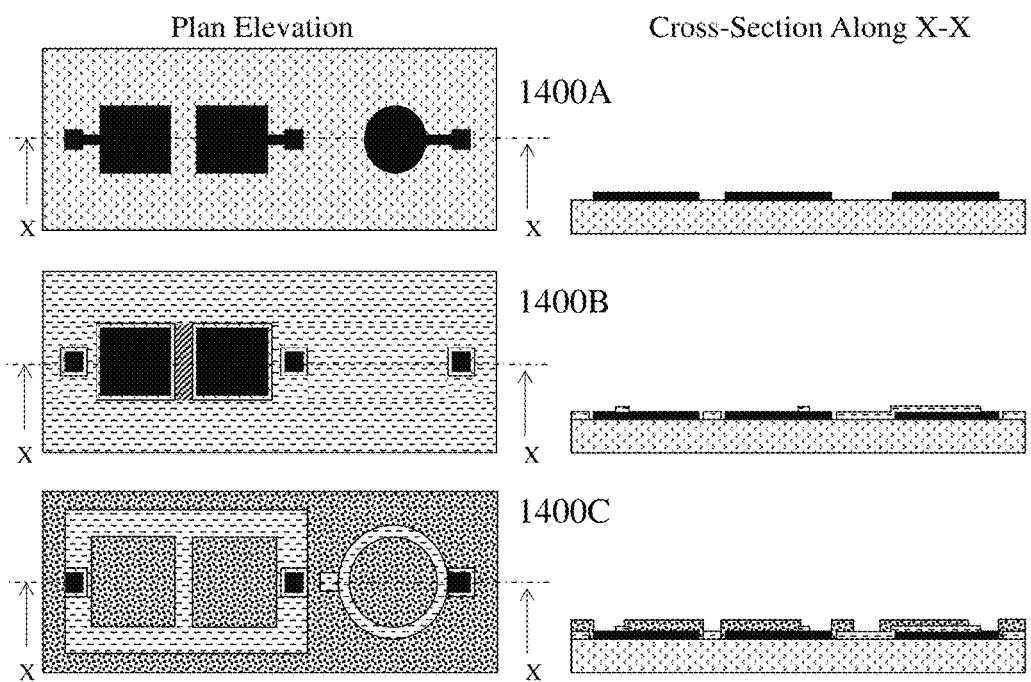
FIGS. 14A and 14B depict a manufacturing sequence for providing multiple measurand capacitive based MEMS sensors for integration atop CMOS electronics according to an embodiment of the invention.
Figure 14B:
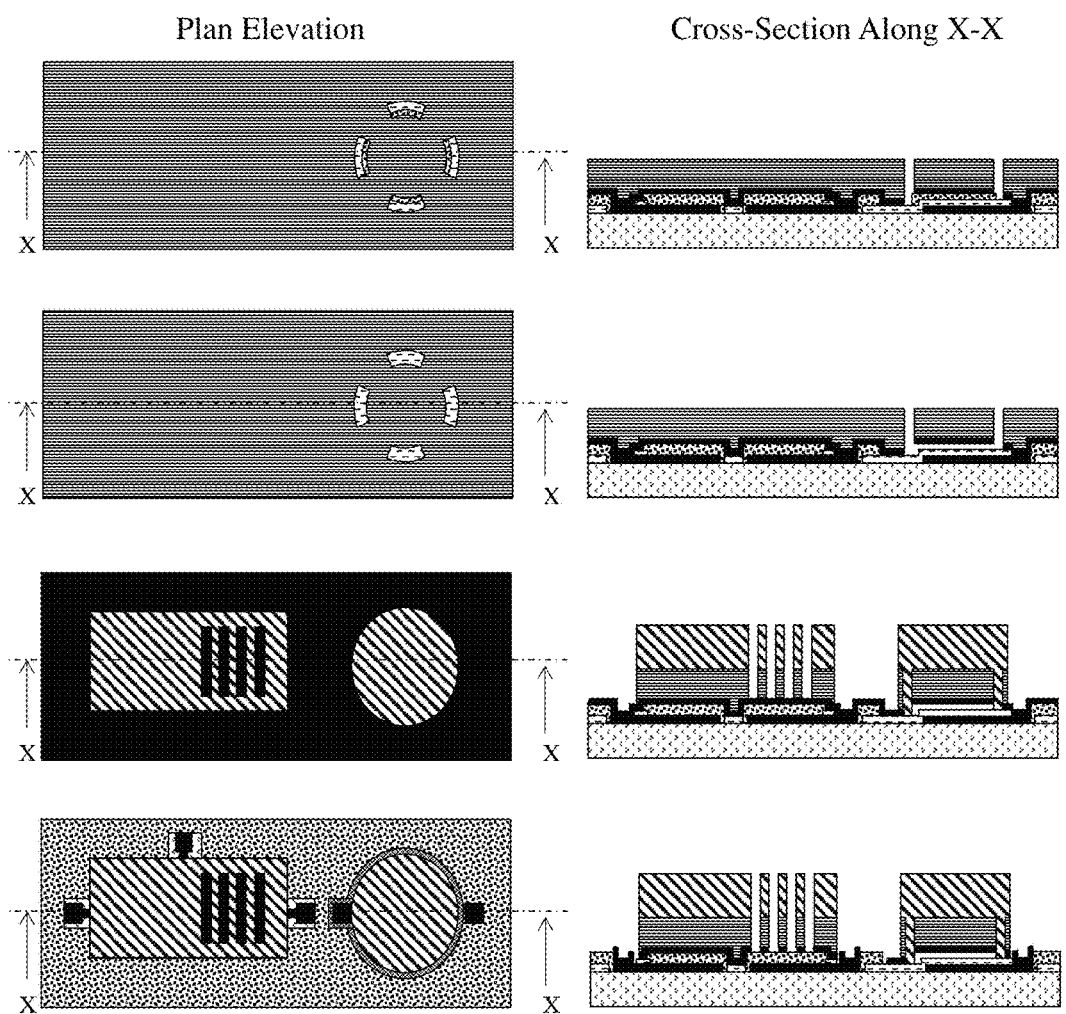

Referring to FIGS. 14A and 14B respectively there are depicted first to seventh process steps 1400A through 1400G respectively for the manufacture of a MEMS based capacitive sensor circuit wherein the processing and manufacturing sequence relates to the fabrication of two electrically-connected humidity sensor elements (i.e., active sensor and reference) together with a pressure sensor. With each of the first to seventh process steps 200A through 200G the multi-measurand capacitive MEMS sensor at these stages of processing is depicted in plan and cross-sectional views. As depicted in the first process step 1400A a passivated silicon 105 substrate, passivated with silicon dioxide ($SiO_2$) 110, has a first layer of metallization deposited, for example 120 nm of DC sputtered aluminum (Al) 120, and etched through wet or dry processing to form the bottom sensing electrodes of the two electrically-connected humidity sensor elements, actual sensor and reference device, together with a pressure sensor. The silicon 105 substrate, not identified explicitly, may for example comprise CMOS electronics or not. According to embodiments of the invention where the silicon 105 substrate contains CMOS electronics the fabrication of two electrically-connected humidity sensor elements and pressure sensor may be performed directly on top of the CMOS electronics, adjacent to the CMOS electronics, or partially overlapping the CMOS electronics.

Next in second process step 1400B a dielectric layer comprising 100 nm of PECVD deposited silicon nitride ($Si_3N_4$) 150 is provided and patterned via a dry etching, i.e. RIE, process to provide an isolation layer atop the bottom electrode for the pressure sensor for pull-in protection. Next, in third step 1400C, a 200 nm polymeric sensing layer 130, is deposited, and dry etched via an oxygen ($O_2$) RIE to form vias for electrical pads. Next a stack of metals and ceramic layers are applied through DC sputtering processes, as depicted in fourth process step 1400D to provide the top sensing electrode for the two electrically-connected humidity sensor elements and their associated protective layer. The ceramic also forming part of the pressure sensor. The metals constitute the electrode and pads, for example these comprise a 10 nm chromium (Cr) 140 adhesion layer and a 200 nm aluminum 120 conductive layer. The ceramic layer(s), for example 500 nm silicon carbide 1 (SiC1) 160 will provide the protective layer to the two electrically-connected humidity sensor elements. In order to provide reliable device operation through self-alignment manufacturing and to reduce the number of masks required, the ceramic, silicon carbide 1 (SiC1), layer(s) is (are) etched first using reactive ion etching (RIE) for example such that the etching process terminates at the top metal layer, in this instance the 200 nm aluminum 120 conductive layer, thereby forming the geometry of the protective layer of the fluid sensor and reference and the geometry of the release holes of the pressure sensor. RIE etching of the silicon carbide 1 (SiC1) layer(s) is made through a 150 nm sputtered chromium 140 mask (not explicitly shown for clarity).

The silicon carbide 160 ceramic layer then serves as a hard mask for the etching of the underlying metals, so as to form the top electrode, for example using PAN, Al, etc. Finally the chromium 140 hard mask is removed using CR-14S etchant. Next in fifth process step 1400E the Sensing Material 130, which acts as sensing layer, in the capacitive fluid sensor elements, and sacrificial layer, in the pressure sensors, is removed wherever it is exposed through the 160 ceramic layer. Accordingly, the pressure sensor MEMS element is released. The release of the pressure sensor is made viable by the controlled low stress of the SiC ceramic material. In sixth process step 1400F a second 500 nm silicon carbide 180 layer is sputtered and processed using another RIE etching process with a 150 nm sputtered chromium ( ) 140 mask (not explicitly shown for clarity) which is patterned using CR-14S wet etch prior to the RIE process and then removed using another CR-14S wet etch process. In these steps the two 500 nm silicon carbide 1 (SiC1) 160 ceramic layers are patterned down to the Al 120 metallization in the active sensor region of the two electrically-connected humidity sensor elements and to pattern the pressure sensor whilst leaving the reference capacitive element of the two electrically-connected humidity sensor elements covered thereby isolating it from the ambient environment of the silicon die containing the two electrically-connected humidity sensor elements and pressure sensor.

Accordingly in seventh step 1400G the Al 120 metallization is etched through a PAN wet etch process (phosphoric, acetic, and nitric acids) thereby isolating the electrodes of the two electrically-connected humidity sensor elements and pressure sensor. It would be evident to one skilled in the art that whilst the Al 120 metallization is depicted within first to seventh process steps 1400A through 1400G respectively in FIGS. 14A and 14B respectively as being patterned to form discrete pads that the metallization may alternatively be routed within the two electrically-connected humidity sensor elements and pressure sensor die to interconnection pads of an underlying, or adjacent, CMOS circuit so that the initial metallization in first process step 1400A connects to these pads. Alternatively, a passivation layer, for example $SiO_2$ 110 or $Si_3N_4$ 150, may be provided between the silicon 105 substrate and its CMOS circuit(s) and the two electrically-connected humidity sensor elements and pressure sensor formed above. In that instance, vias may be provided through the passivation layer to connect the CMOS circuit(s) and the two electrically-connected humidity sensor elements and pressure sensor.

It would be evident to one skilled in the art that optionally the sacrificial layer and sensing element may be formed from different materials rather than the same material as depicted above in respect of FIGS. 14A and 14B respectively. It would also be evident that the top electrode geometry of the fluid sensor or the release holes of the pressure sensor can be varied to attain different device characteristics without modifications of the sequence depicted in seventh process step 1400G. It would be similarly evident that the electrode geometry within other sensors, such a humidity sensor for example, may also be varied in order to optimize device performance with respect to one or more characteristics.

Figure 15:
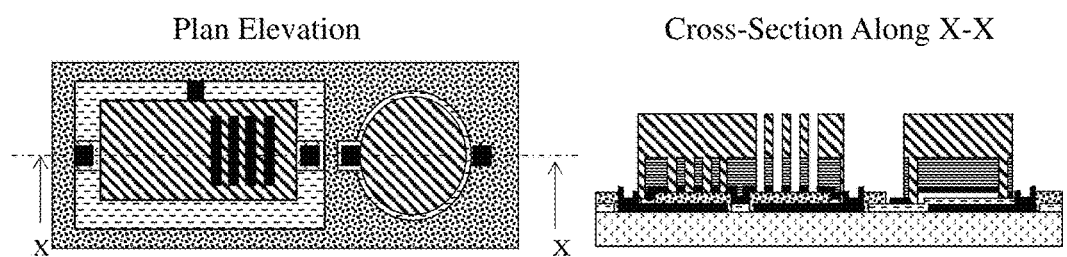
FIGS. 15 to 18 depict multiple measurand capacitive based MEMS sensors for integration atop CMOS electronics according to another embodiment of the invention.

Now referring to FIG. 15 there is depicted a multiple measurand capacitive based MEMS sensors for integration atop CMOS electronics according to another embodiment of the invention. In contrast to the multiple measurand capacitive based MEMS sensor die depicted in seventh process step 1400G in FIG. 14B wherein the initial silicon nitride 150 layer was patterned during earlier process steps to form the same pattern on both the reference and active elements of the two electrically-connected humidity sensor elements allowing for better reference and active sensor matching, and the aluminum 120 etched. Then the silicon carbide 2 180 is deposited and patterned thereby capping the reference element and the pressure sensor.

Figure 16:
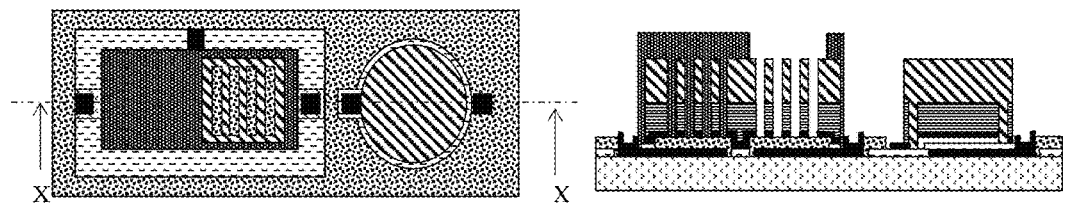

Now referring to FIG. 16 there is depicted a multiple measurand capacitive based MEMS sensors for integration atop CMOS electronics according to another embodiment of the invention. In contrast to the multiple measurand capacitive based MEMS sensor die depicted in seventh process step 1400G in FIG. 14B wherein the initial silicon nitride 150 layer was patterned during earlier process steps to form the same pattern on both the reference and active elements of the two electrically-connected humidity sensor elements, and the aluminum 120 etched. Then the silicon carbide 2 180 was deposited and patterned thereby capping the pressure sensor and patterning the active and reference elements of the two electrically-connected humidity sensor elements. Subsequently a parylene 170 encapsulating layer was deposited through vapour deposition and patterned to seal the reference element within the two electrically-connected humidity sensor elements.

Figure 17:
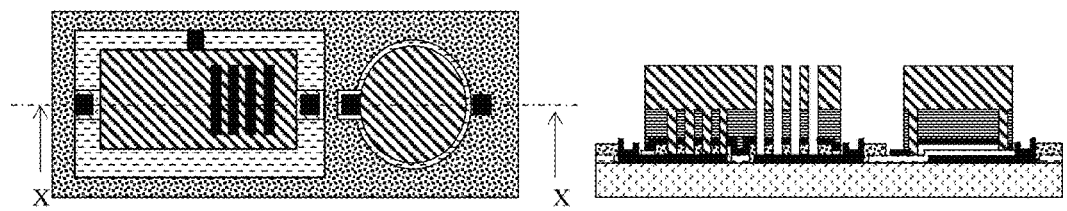
Figure 18:
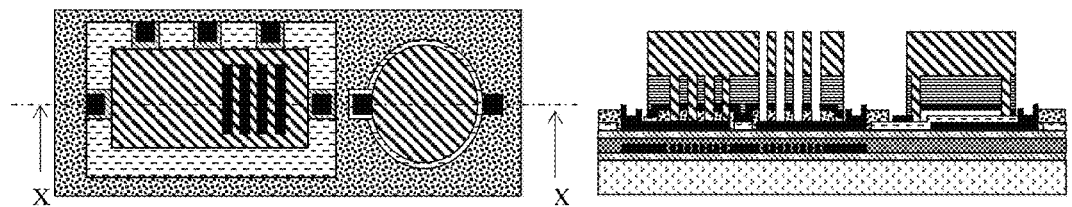

Referring to FIG. 17 there is depicted a multiple measurand capacitive based MEMS sensors for integration atop CMOS electronics according to another embodiment of the invention wherein the silicon carbide 2 (SiC2) 180 caps the reference element but wherein the sensing layer, Sensing Material 130, was patterned during previous processing steps such that it was etched out in the regions corresponding to openings within the silicon carbide 1 (SiC1) 160 and SiC2 180 thereby increasing exposure of the sensing layer to the ambient humidity in this instance, or fluid to be sensed in other embodiments. Likewise in FIG. 18 there is depicted a multiple measurand capacitive based MEMS sensors for integration atop CMOS electronics according to another embodiment of the invention wherein a pair of heater elements have been formed beneath the two electrically-connected humidity sensor elements via deposition and etching of an aluminum 120 film within a dielectric stack comprising lower and upper aluminum 110 and intermediate silicon nitride ($Si_3N_4$) 150.

Accordingly, it would be evident to one skilled in the art that the etching of the sensing film layer, in this instance Sensing Material 130, provides for narrow elongated sensing elements in an array form with increased surface area of exposure and an efficient diffusion path across the sensing layer, as the film sidewalls are now exposed in addition to the top surface of the sensing film, but importantly diffusion can occur through the full thickness of the sensing film thereby increasing the speed of detecting variations in the material being sensed. Additionally, the heater elements allow for temperature stabilization as well as beneficially operating the capacitive sensors at elevated temperature wherein the diffusion constant is increased further, thereby further increasing the speed of the capacitive sensor element. Additionally, heater elements allow for driving the sensed fluid from the capacitive sensor elements, e.g. dehydration for a humidity sensor, thereby limiting saturation or allowing recovery from saturation of the sensing layer.

Figure 19A:
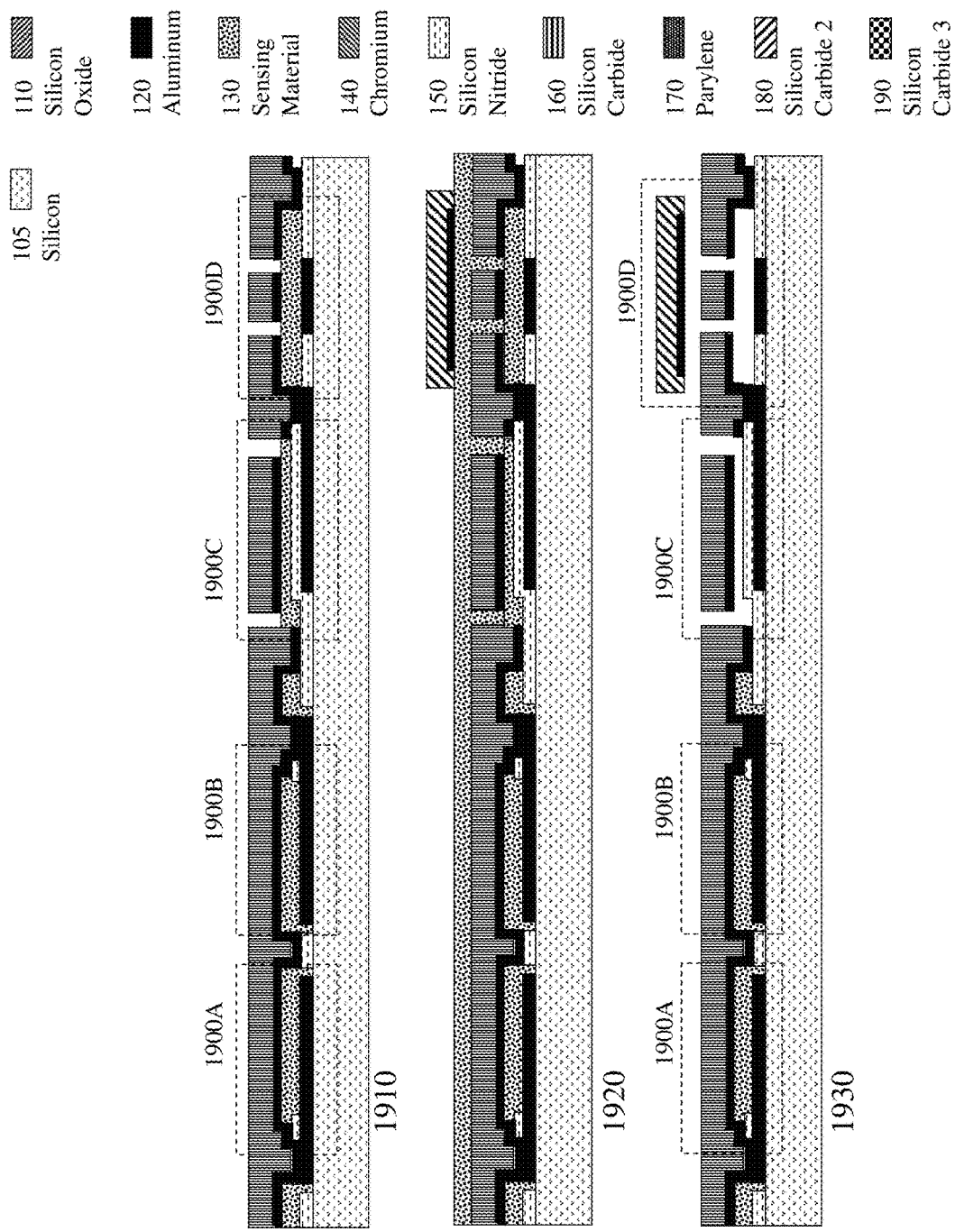
FIGS. 19A and 19B depict an alternate back end processing sequence for providing multiple measurand capacitive based MEMS sensors for integration atop CMOS electronics according to an embodiment of the invention.
Figure 19B:
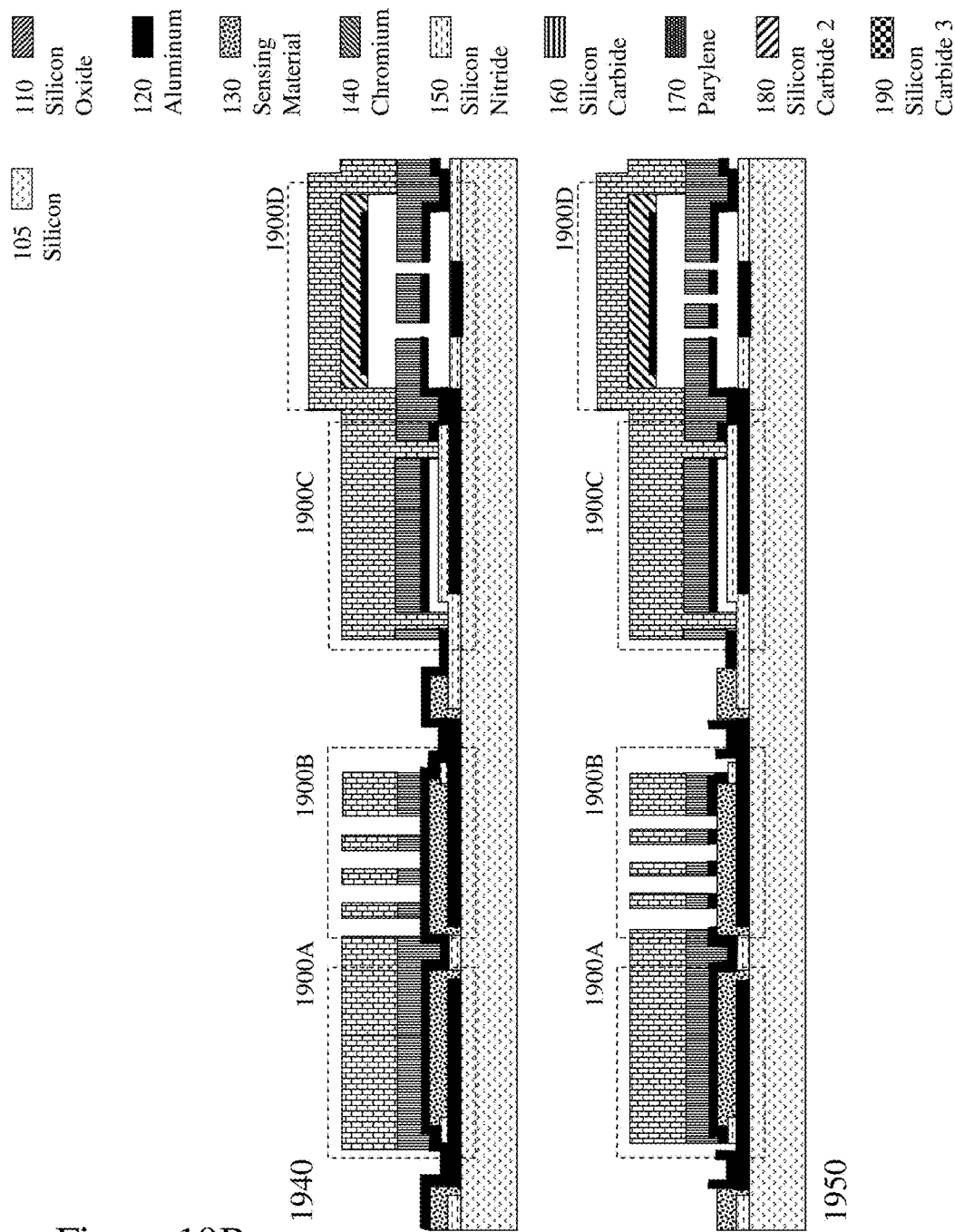

Now referring to FIGS. 19A and 19B respectively, there are depicted first to fifth process steps 1910 through 1950 respectively in respect of a multi-measurand capacitive sensor according to an embodiment of the invention. As depicted in first process step 1910 a pair of fluid sensing elements 1900A and 1900B have been initiated to the left hand side of the die, a pressure sensor 1900C and suspended clamped beam resonator 1900D are being initiated at the right hand side of the die. At first step the lower electrode in aluminum 120, isolating dielectric silicon nitride ($Si_3N_4$) 150, sensing layer/sacrificial layer Sensing Material 130, and first ceramic silicon carbide 1 (SiC1) 160 have been deposited and patterned. Next in second process step 1920 the structure is planarised with a second layer of Sensing Material 130 atop which a third metallization aluminum 120 and second silicon carbide 2 (SiC2) 180 deposited the silicon carbide 2 (SiC2) 180 patterned. Accordingly in third process step 1930 the Sensing Material 130 has been etched thereby releasing the MEMS elements of the pressure sensor 1900C and clamped beam resonator 1900D as well as the capping of the silicon carbide 2 (SiC2) 180.

Next in fourth process step 1940 a third ceramic layer silicon carbide 3 (SiC3) 190 is deposited thereby completing the pressure sensor 1900C, further capping the reference capacitive based fluid sensor element 1900A, and sealing the clamped beam resonator 1900D within the environment present during the deposition of the third ceramic layer silicon carbide 3 (SiC3) 190, namely a very low pressure. Next in fifth process step 1950 the metallization aluminum 120 is etched isolating the electrical patterns of the multiple devices. Optionally, the silicon carbide 3 (SiC3) 190 may be deposited in two stages with different ambient environments in order to seal the pressure sensor 1900C and clamped beam resonator 1900D at different pressures.

It would be evident to one skilled in the art that the process flows presented supra in respect of first to seventh process steps 1400A through 1400G in FIGS. 14A and 14B respectively and first to fifth process steps 1910 through 1950 in FIGS. 19A and 19B respectively represent an improvement over the prior art such as presented for example by Cicek et al in "Design of a Low Cost MEMS Monolithically Integrated Relative Humidity Sensor" (Proc. Int. Conf. Microelectronics 2010, pp. 172-175) and Hong et al in "High sensitivity capacitive humidity Sensor with a Novel Polyimide Design Fabricated by MEMS Technology" (4th IEEE Nano/Micro Engineered and Molecular Systems, 2009, pp 703-706) wherein humidity sensors are integrated onto a silicon 105 substrate using upper and lower electrodes with a Sensing Material 130 sensing layer but without any ceramic structures for self-aligned processing and/or protection against chemical and physical contaminants nor compatibility with simultaneous fabrication of other capacitance based MEMS sensors.

Referring to FIG. 20 there are predicted first and second cross-sections 2010 and 2020 for a capacitive based fluid sensor according to an embodiment of the invention. As discussed within the prior art, see for example Cicek and Hong, enhanced performance can be obtained from etching beneath the capacitive sensing elements, to provide a cavity, thereby allowing faster propagation of the fluid into the sensing layer. However, for integrating MEMS above CMOS electronics etching into the silicon 105 requires that the MEMS capacitive sensing element be placed in a region of the silicon die without CMOS electronics thereby increasing die footprint. However, according to embodiments of the invention ceramic MEMS structural element may be manufactured directly atop CMOS electronics (above-IC) in released form through deposition of a sacrificial material prior to the deposition of the ceramic MEMS structural element(s).

Accordingly as depicted in first cross-section 2010 taken along Section Y-Y an array of sensing elements 2030 are provided via a process flow according to an embodiment of the invention wherein from the bottom to the top the sensing element 2030 comprises first metallization (aluminum 120), first ceramic (silicon carbide 1 160), second metallization (aluminum 120), Sensing Material 130, and third metallization (aluminum 120). As depicted one group of sensing elements 2030 are free allowing fluid movement around and absorption whilst another group of sensing elements 2030 are isolated using parylene 170 to provide the reference sensing element such as described above in respect of FIGS. 2 through 19. Optionally process flows according to other embodiments of the invention allow for the fabrication of adjacent reference and sensing elements wherein the reference device may be formed from a continuous sensing film, sectioned as per the sensing element, and coated with second ceramic deposition (silicon carbide 2 180) or a combination thereof.

As evident from second cross-section 2020 representing Section X-X the sensing elements 2030 in this embodiment of the invention are implemented as a standing beam supported at either end, made viable by the controlled low stress of the SiC ceramic material. Within the sensing elements 2030 first metallization (aluminum 120) provides the heater element on each sensing element 2030 whilst second and third metallizations (aluminum 120) provide the upper and lower electrodes of the capacitive sensing element. As depicted the reference and sensing elements of the capacitive-based MEMS fluid sensor are integrated above CMOS electronics 2030 without micromachining of the silicon 105 beneath the capacitive based MEMS fluid sensor as required within the prior art. Accordingly fully surrounded fluid sensing elements may be implemented directly atop CMOS electronics with ceramic supporting structural members.

Now referring to FIG. 21 there is depicted a multifunction circuit according to an embodiment of the invention. As depicted the circuit comprises a reference humidity element 2100A, humidity sensor 2100B, pressure sensor 2100C, clamped beam resonator 2100D, tuning fork gyroscope 2100E, reference flow sensor 2100F and flow sensor 2100G. It would be evident to one skilled in the art that the tuning fork gyroscope may alternatively be a different microelectromechanical gyroscope, including but not limited to, a frame gyroscope, a coupled-mass gyroscope, a 3-DOF or 4-DOF micro-gyroscope, a ring micro-gyroscope, a vibrating ring gyroscope, suspended disc dual-axis gyroscope, and a bulk acoustic wave gyroscope. It would also be evident that some elements such as reference flow sensor 2100F and flow sensor 2100G for example may be replicated several times with different active sensor layers in each to provide measurements of multiple fluids or components of fluids or other sensed quantities (e.g., motion, pressure) simultaneously. Accordingly, such circuits would allow real-time measurement of blood chemistry for example at the same time as environmental factors such as temperature, pressure and humidity with tracking of motion and/or position.

Figure 22:
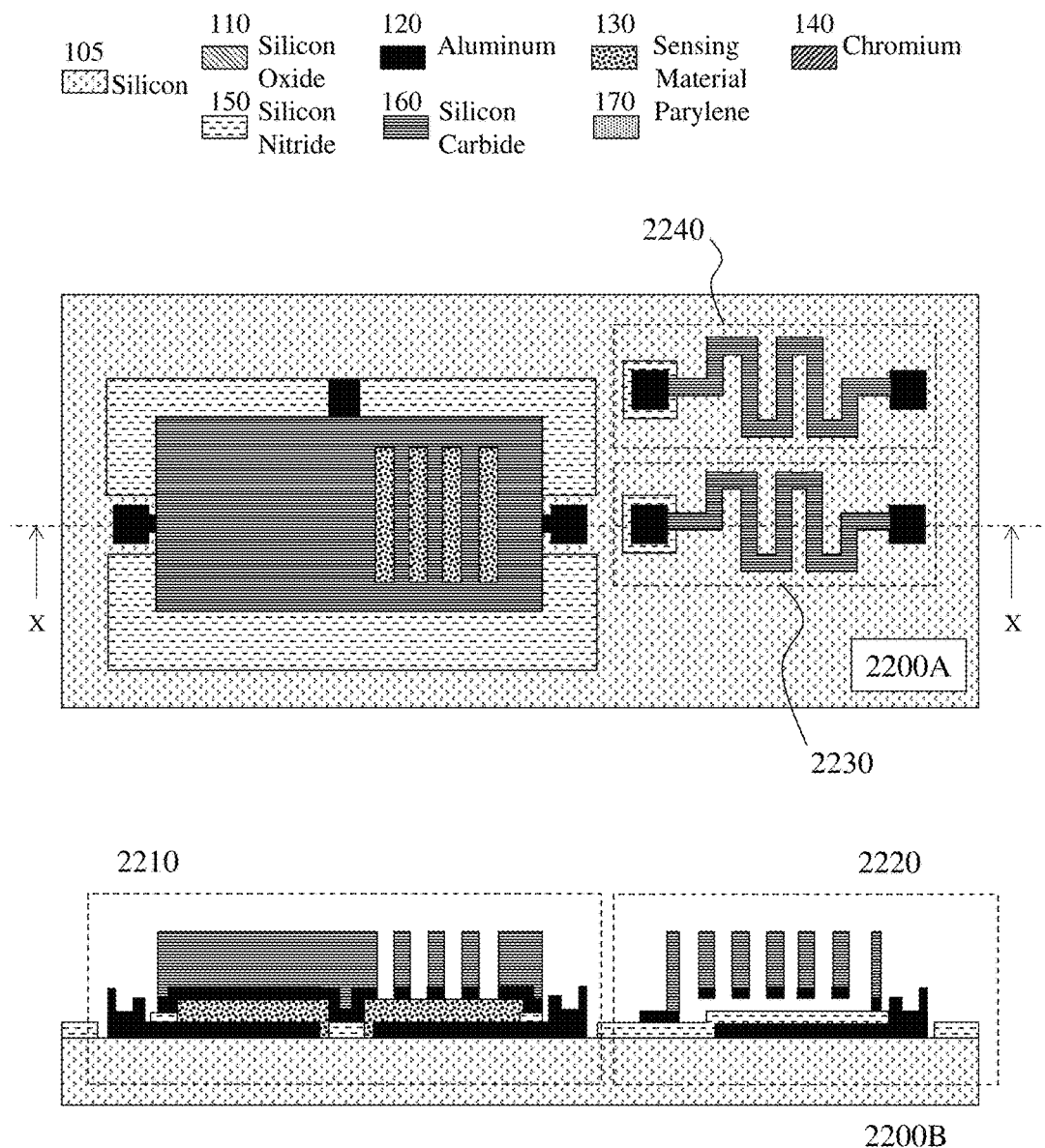
FIG. 22 depicts a humidity and Pirani gauge pressure sensing circuit according to an embodiment of the invention.

Referring to FIG. 22 there is depicted a multi-measurand MEMS circuit comprising a humidity sensor 2210 with integrated sealed reference and a Pirani gauge pressure sensor 2220 according to an embodiment of the invention. As depicted a heater element 2230 formed from an aluminum 120 resistance element on the lower side of a silicon carbide 160 ceramic structure is disposed upon the silicon 105 substrate. When heated the heater element 2230 loses heat to gas molecules which collide with it and remove heat. Accordingly, as the gas pressure is reduced the number of molecules present will fall proportionately and the wire will lose low heat more slowly such that the heat loss is an indirect indication of pressure. As the electrical resistance of the heater element 2230 will also vary with temperature, so the resistance indicates the temperature of wire and in many cases the heater element 2230 is maintained at a constant resistance R by controlling the current I through the wire. The resistance can be measured using a bridge circuit, such as known within the prior art, employing integrated resistors 2240 within the multi-measurand MEMS circuit.

Figure 23:
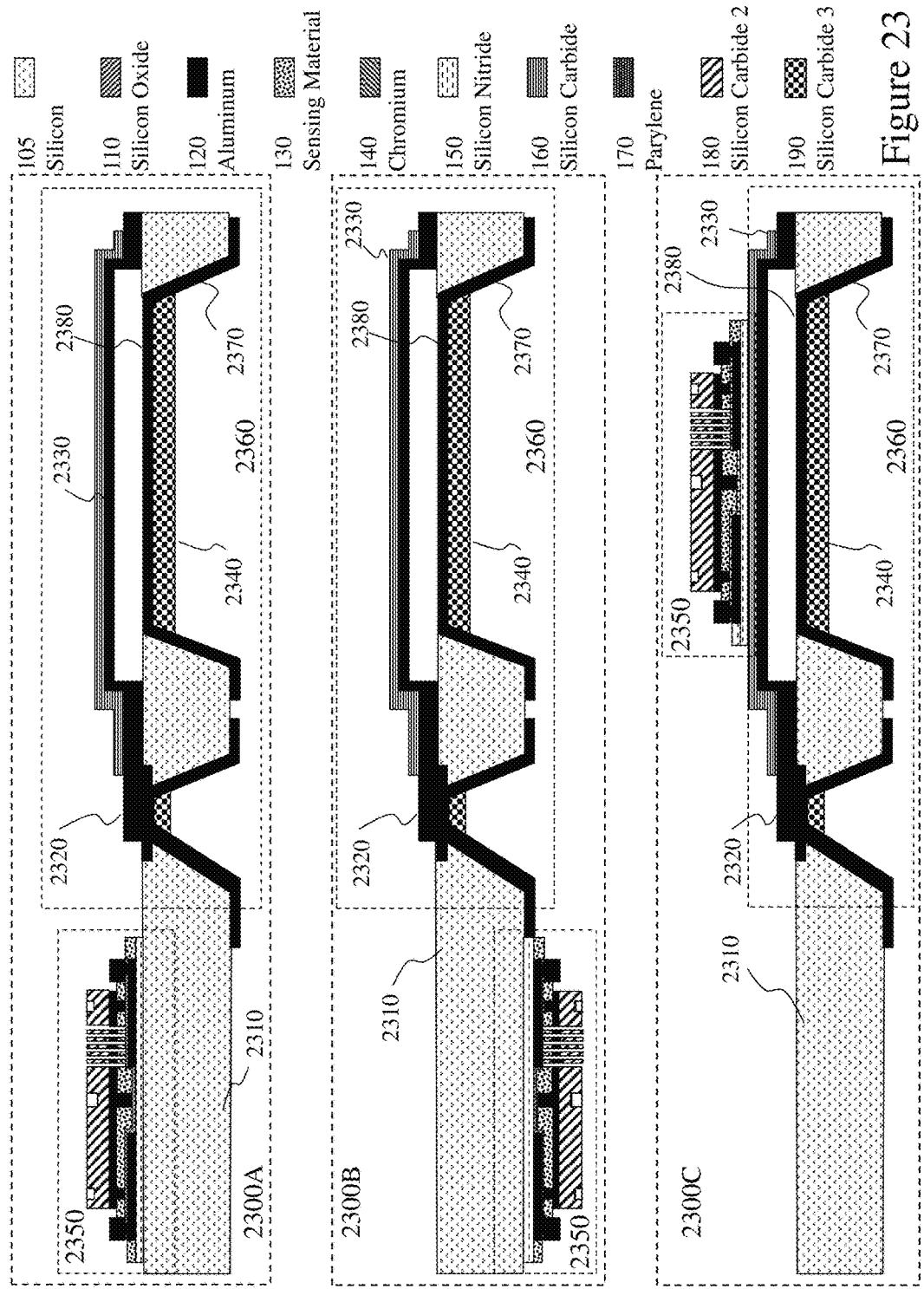
FIG. 23 depicts MEMS based humidity sensors integrated with bulk-process MEMS devices according to embodiments of the invention.

Now referring to FIG. 23 there are depicted first to third MEMS devices 2300A to 2300C respectively employing thin film MEMS humidity sensors 2350 with first integrated with bulk-process MEMS devices 2360 according to embodiments of the invention. In first MEMS device 2300A the thin film MEMS humidity sensors 2350 is integrated on the opposite surface of the silicon wafer 2310 to the recess machined into the silicon wafer 2310 that forms part of the with bulk-process MEMS devices 2360. In second MEMS device 2300B the thin film MEMS humidity sensors 2350 is integrated on the same surface of the silicon wafer 2310 as the recess machined into the silicon wafer 2310 that forms part of the with bulk-process MEMS devices 2360. In third MEMS device 2300B the thin film MEMS humidity sensors 2350 is integrated onto the upper ceramic 2330, silicon carbide 160, which forms part of the bulk-process MEMS devices 2360. In each of the first to third MEMS devices 2300A to 2300C respectively the bulk-process MEMS devices 2360 comprises a recess with first metallization 2370 is formed upon the sidewalls of the recess, a predetermined portion of the recess is filled with lower ceramic 2340, silicon carbide 160. Subsequently, second metallization 2370 has been deposited onto lower ceramic 2340 interconnecting with first metallization 2370. Formed above this region is a hermetic cover comprising third metallization 2320 and upper ceramic 2330. This hermetic encapsulation can also be implemented via a capping layer accomplished via wafer bonding such as suggested in prior art, see for example El-Gamal et al in U.S. Pat. No. 8,409,901 entitled "Low temperature wafer level processing for MEMS devices.

Within descriptions presented supra in respect of some embodiments of the invention in FIGS. 2 through 23 two or three ceramic layers identified as silicon carbide 1 (SiC1) 160, silicon carbide 2 (SiC2) 180 and silicon carbide 3 (SiC3) 190 are employed. However, within other embodiments of the invention presented supra these may be replaced by two or more layers of different materials, such that for example the lower layer, SiC1 in the embodiments described, is maintained but that the second SiC2 layer is replaced with another material such as Parylene 170 or another material such as another ceramic, silicon dioxide 110, silicon nitride 150, silicon oxynitride, noble metals, spin-on glass, and barrier metals.

Within the preceding descriptions in respect of FIGS. 2 through 23 the focus has been to the design, manufacturing and implementation of sensors, particularly capacitance based sensors, discretely or in combination with CMOS electronics. However, it would be evident that in some embodiments of the invention the presence of a ceramic layer, such as silicon carbide (SiC), provides additional benefits in terms of post-processing of the sensor wafer. For example, this ceramic layer may provide protection for the sensing layer during back-grinding of the wafer to achieve a thinner package in either MEMS-above-CMOS or MEMS-only solutions. This protective layer can also enhance the robustness of the sensing layer to the packaging operation, which can be advantageous to reduce costs and increase yields of the packaging operation. Accordingly, the ceramic layer may also serve as protection during a molded packaging process, such as film-assisted molding or transfer molding for example or even just molding with an insert to create an opening in the package.

Within the embodiments of the invention described above in respect of FIGS. 2 through 23 a reference capacitive sensing element has been described as being hermetically sealed through the use of one or more materials which may be selected from the group of materials including but not limited to silicon carbide 160, another ceramic, silicon dioxide 110, silicon nitride 150, silicon oxynitride, parylene 170, noble metals, spin-on glass, and barrier metals. It would be evident that the degree of hermeticity may vary in dependence upon one or more factors including, but not limited to, the fluid being sensed; the ceramic composition, porosity, thickness etc.; the sensor geometry; operating environment; anticipated lifetime of sensor; acceptable failure rate; and acceptable calibration error. Accordingly in some embodiments of the invention the reference capacitive sensing element is formed during the same manufacturing sequence as the capacitive sensing element but without patterning such that the ceramic, e.g., acts as the barrier without additional processing or is patterned directly thereover with a noble metal or barrier metal for example. As the surface area of the reference capacitive sensing element may now differ from that of the capacitive sensing element an adjustment of the calibration derived from the reference capacitive sensing element by the CMOS electronics may be implemented or the area of the reference capacitive sensing element may be adjusted accordingly to make them approximately equivalent.

Beneficially embodiments of the invention provide a fabrication process which is designed to be fully compatible with CMOS electronics, and other electronics technologies that can withstand the low processing temperatures of embodiments of the invention. Beneficially this provides for direct integration over the electronics; improved system performance through reduced parasitic effects; reduced die size; reduced package footprint and thickness; self-aligned processing; lower sensor fabrication costs through batch processing; integral reference elements; and integral heaters and/or temperature stabilization.

Within the preceding disclosure primary consideration has been given to the design, fabrication and implementation of capacitive sensors exploiting low temperature ceramic structures. However, within the descriptions in respect of these embodiments of the invention it is noted that the ceramic structures, e.g. SiC1 160 or SiC2 180, provide for self-aligned processing of the MEMS structures. For example in FIGS. 3A and 3B the SiC1 160 or in FIG. 5 the SiC1 160 and SiC2 180 provide self-aligned masking for additional processing steps. In respect of FIGS. 3A and 3B and 5 respectively these steps represent the etching of the upper electrode and upper electrode/sensing layer respectively. However it would be evident to one skilled in the art that the self-aligned masking provided by the patterned ceramic may be employed for etching one or more layers within a MEMS structure including, but not limited to, another ceramic layer, dielectrics, metallization, sensing layers, and the substrate.

Within the preceding disclosure capacitance based humidity sensors have been described in a variety of configurations from discrete devices, combined sensor—reference device pairs, and as part of multiple measurand MEMS sensor devices. Within these descriptions the sensing layer has been described as being a Sensing Material 130. It would be evident that Sensing Material 130 may be provided by a single material or by multiple materials selected from the group comprising a polymer, a cross-linked polymer, cellulose acetate butyrate, polyimide, cross-linked polyimide, polysulfone, poly(methyl methacrylate) (PMMA), poly9vinyl crotonate), poly(ethyleneterephthalate), chemical vapor deposited teflon, plasma polymerized $C_4F_8$, and a mending of polyimide and polysulfone, see for example Rafiq et al in "Kinetics of Thermal Degradation of Polysulfone/Polyimide Blended Polymeric Membranes" (J. App. Polymer Sci., Vol. 123, pp. 3755-3763).

Within the embodiments of the invention described above capacitive sensor elements have been described as discrete MEMS elements or in conjunction with other MEMS elements such as pressure sensors and Pirani pressure gauges. In other embodiments of the invention humidity sensors operating in conjunction with or in isolation to MEMS capacitive sensor elements may be employed including, for example, polymeric resistive humidity sensors exploiting polyelectrolytes and conjugated polymers.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

What is claimed is:

1. A device comprising:
  a substrate;
  a series of layers disposed within a first predetermined region of the substrate comprising a lower electrode layer of a first electrically conductive material closest to the substrate, a sensing layer of a predetermined material disposed atop the lower electrode, an upper electrode layer of a second electrically conductive material disposed atop the sensing layer, and a ceramic layer disposed above the upper electrode layer;
  a first capacitive based sensor formed vertically within the series of layers comprising the lower electrode layer, the sensing layer, and the upper electrode layer;
  a barrier formed from a predetermined barrier material covering a first predetermined portion of the first capacitive based sensor thereby providing protection for the first predetermined portion of the first capacitive based sensor; wherein
  the predetermined material is selected in dependence upon a predetermined characteristic of the predetermined material varying in dependence upon an amount of a predetermined fluid that it is exposed to such that the capacitance of the first capacitive based sensor employing the predetermined material varies in dependence upon the amount of the predetermined fluid that the predetermined material within the first capacitive based sensor is exposed to.

2. The device according to claim 1, wherein
the ceramic layer is formed a material selected from the group comprising silicon carbide, alumina, aluminum nitride, silicon nitride, silicon oxynitride and diamond.

3. The device according to claim 1, wherein
the predetermined material of the barrier is selected from the group comprising silicon carbide, alumina, aluminum nitride, silicon nitride, silicon oxynitride, diamond, a spin-on glass, silicon nitride, silicon oxide, a noble metal, a chemical vapor deposited poly(p-xylylene) polymer (parylene), a barrier metal, and a material impervious to the predetermined fluid.

4. The device according to claim 1, wherein
the barrier and ceramic layer are formed from the same material, the material selected from the group comprising silicon carbide, alumina, aluminum nitride, silicon nitride, silicon oxynitride and diamond.

5. The device according to claim 1, wherein
the first capacitive based sensor comprises:
  a predetermined pattern formed within the lower electrode;
  a predetermined pattern formed within the sensing layer;
  a predetermined pattern formed within the upper electrode comprising at least a plurality of openings within the upper electrode; and
  a predetermined pattern formed within the ceramic layer comprising at least a plurality of holes within the ceramic layer fluidically connected to the openings in the upper electrode; and
the first predetermined portion of the first capacitive sensor covered by the barrier does not cover the holes within the ceramic layer allowing the predetermined fluid to flow to the sensing layer via the holes within the ceramic layer and the openings in the upper electrode.

6. The device according to claim 1, further comprising
a bottom electrode formed within a third electrically conductive material disposed below the first capacitive sensor; wherein
the third electrically conductive material is electrically isolated from the first electrically conductive material by a dielectric layer.

7. The device according to claim 1, wherein
the barrier is disposed between the upper electrode layer and the ceramic layer.

8. The device according to claim 1, wherein
the first capacitive based sensor is an active sensor for measuring an amount of the predetermined fluid within fluidic pathways formed within the upper electrode, ceramic layer allowing the sensing layer within the first capacitive based sensor to be fluidically connected to an external environment around the device;
the barrier is disposed between the lower electrode and the sensing layer; and
a second barrier formed from a second predetermined barrier material is disposed between the sensing layer and the upper electrode in those regions of the first capacitive based sensor not providing fluidic pathways between the external environment and the sensing layer and upon the sidewalls of the fluidic pathways through the upper electrode layer and ceramic layer.

9. The device according to claim 1, wherein
the sensing layer within the first capacitive based sensor has been removed in the regions beneath a plurality of fluidic pathways each comprising an opening formed within the upper electrode which is fluidically connected to a hole within the ceramic layer; and the sensing layer within a second capacitive based sensor is not patterned.

10. The device according to claim 1, further comprising a capacitive based microelectromechanical systems (MEMS) device selected from the group comprising a fixed capacitor, a clamped beam resonator, a gyroscope, and a pressure reference; wherein
the capacitive based MEMS element employs the ceramic layer as a structural layer of the capacitive based MEMS device.

11. The device according to claim 1, further comprising a capacitive based MEMS device selected from the group comprising a fixed capacitor, a clamped beam resonator, a gyroscope, and a pressure reference; wherein
the capacitive based MEMS element employs the ceramic layer as a structural layer of the capacitive based MEMS device; and
the capacitive based MEMS element is encapsulated by the barrier layer.

12. The device according to claim 1, further comprising a complementary metal-oxide-semiconductor (CMOS) integrated circuit disposed within the substrate beneath a first predetermined portion of the first capacitive based sensor.

13. The device according to claim 1, further comprising:
a second ceramic layer disposed beneath the series of layers; wherein
the series of layers are formed upon a second ceramic layer.

14. The device according to claim 1, wherein either:
the sensing layer is a single material selected from the group comprising a polymer, a cross-linked polymer, cellulose acetate butyrate, polyimide, cross-linked polyimide, polysulfone, poly(methyl methacrylate) (PMMA), poly9vinyl crotonate), poly(ethyleneterephthalate), chemical vapor deposited teflon, plasma polymerized $C_4F_8$ and a polyimide/polysulfone blend; or
the sensing layer comprises two or more materials, each material selected from the group comprising a polymer, a cross-linked polymer, cellulose acetate butyrate, polyimide, cross-linked polyimide, polysulfone, poly(methyl methacrylate) (PMMA), poly9vinyl crotonate), poly(ethyleneterephthalate), chemical vapor deposited teflon, plasma polymerized $C_4F_8$ and a polyimide/polysulfone blend.

* * * * *